(12) United States Patent
Goldstein et al.

(10) Patent No.: US 6,350,757 B1
(45) Date of Patent: Feb. 26, 2002

(54) BETA-CARBOLINE COMPOUNDS

(75) Inventors: Solo Goldstein, Suresnes; Guillaume Poissonnet, Orsay; Jean-Gilles Parmentier, Issy les Moulineaux; Jean-Daniel Brion, Saint Leu la Foret; Mark Millan, Le Pecq; Anne Dekeyne, Saint Remy les Chevreuses; Jean Boutin, Suresnes, all of (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 09/621,742

(22) Filed: Jul. 21, 2000

(30) Foreign Application Priority Data

Jul. 23, 1999 (FR) .............................................. 99.09576

(51) Int. Cl.[7] .............................................. C07D 471/14
(52) U.S. Cl. .......................... 514/292; 546/85; 546/86; 546/87
(58) Field of Search ............................ 514/292; 546/85, 546/86, 87

(56) References Cited

U.S. PATENT DOCUMENTS 5,300,645 A * 4/1994 Audia et al. .................. 546/49

* cited by examiner

*Primary Examiner*—Patricia L. Morris

(74) *Attorney, Agent, or Firm*—The Firm of Hueschen and Sage; G. Patrick Sage

(57) ABSTRACT

A compound selected from those of formula (I):

wherein:
=== represents single or double bond,
$R_1$ represents hydrogen, alkyl, —$R_6$-aryl, —$R_6$-cycloalkyl, —$R_6$-heterocycle, —$CO_2R_7$—, —$COR_8$, or —$CONHR_8$, wherein $R_6$, $R_7$, and $R_8$ are as defined in the description,
$R_2$ represents cyano, mono- or di-alkylaminoalkylaminocarbonyl, —$CO_2R_8$, —$CONHR_8$, —$NR_8R_9$, —$NHCO_2R_7$, or —$COR_8$ wherein $R_7$, $R_8$, and $R_9$ are as defined in the description,
$R_3$ and $R_4$ together form ($C_3$–$C_{10}$)cycloalkyl,
$R_5$ represents hydrogen, alkyl, or arylalkyl,
Ra, Rb, Rc, Rd, which may be identical or different, represent a group as defined in the description,
its isomers, and pharmaceutically-acceptable acid or base addition salts thereof, and medicinal products containing the same which are useful in the treatment of CNS disorders.

21 Claims, No Drawings

BETA-CARBOLINE COMPOUNDS

FIELD OF THE INVENTION

The present invention relates to new β-carboline compounds, and to pharmaceutical compositions containing them. The new compounds have a serotonergic activity on receptors of the 5-HT$_2$ family.

Serotonin is a neurotransmitter that acts on 5-HT (5-hydroxytryptamine) receptors both centrally and peripherally. To date, fourteen sub-types of serotonin receptor have been identified and classified within seven families, 5-HT$_1$ to 5-HT$_7$. Of the 5-HT$_2$ family, the sub-types 5-HT$_{2A}$, 5-HT$_{2B}$ and 5-HT$_{2C}$ are known. Those sub-types play a similar role in their specificity for a large number of ligands (Trends. Pharmacol. Sci., 1995, 16, 105–110, Neuropharmacology, 1994, 33, 275–317).

Since the compounds are capable of modulating the activity of 5-HT$_2$ receptors and especially of 5-HT$_{2C}$ and 5HT$_{2B}$ receptors they are likely to be of use in the treatment of complaints such as sleep disorders, (Psychopharmacology, 1989, 97, 436–442; Neuropharmacol., 1994, 33, 467–471), appetite disorders (Psychopharmacology, 1997, 133, 309–312), panic attacks, phobias, anxiety (Br. J. Pharmacol., 1996, 117, 427–434; Neuropharmacology, 1997, 36, 793–802), depression (Biol. Psychiatry, 1996, 39, 1000–1008; Neuroscience, 1999, 91(2), 587–597), impulsive and aggressive disorders (Pharm. Biochem. Behavior, 1991, 39, 729–736), sexual disorders (Clinical Neuropharmacology, 1997 20(3), 210–214), migraine (Progress in Drug Research, 1998, 51, 219–244, ed. Springer Verlay), schizophrenia and psychosis (Eur. J. Pharm., 1993, 245, 179–182; Biol. Psychiatry, 1998, 44, 1099–1117).

PRIOR ART DESCRIPTION

A large number of β-carboline compounds have already been described in the literature. That applies more especially to Patent Application EP 0 620 223, which claims tetrahydro-pyrido-indole compounds, those compounds having a strong affinity for 5-HT$_{2C}$ receptors. The Patent Applications EP 0 320 079 and EP 0 300 541 claim β-carboline compounds, dihydro-β-carboline and tetrahydro-β-carboline, which have a strong fibrinolytic activity. Finally, Patent Application WO 95/24200 describes compounds having in particular a tetrahydro-β-carboline structural pattern. Those compounds are specific antagonists of 5-HT$_{2B}$ receptors.

In addition to the fact that the compounds of the present invention are new, they have proved to be potent selective ligands of 5-HT$_2$ receptors and, in particular, of 5-HT$_{2C}$ and 5HT$_{2B}$ antagonists, thus rendering them potentially useful in the treatment of depression, psychosis, schizophrenia, phobia, anxiety, panic attacks, sleep disorders, appetite disorders, impulsive and aggressive disorders, sexual disorders and migraine.

DETAILED DESCRIPTION OF THE INVENTION

The present invention relates more specifically to compounds of formula (I):

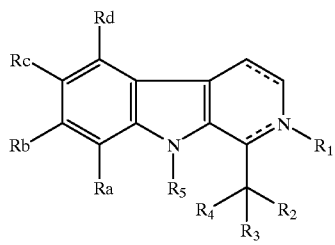

wherein:
==== represents a single or double bond capable optionally of conferring an aromatic character to the ring carrying them, R$_1$ represents a group selected from:
  hydrogen,
  linear or branched (C$_1$–C$_6$)alkyl,
  —R$_6$-aryl, —R$_6$-cycloalkyl, —R$_6$-heterocycle, in which groups R$_6$ represents a linear or branched (C$_1$–C$_6$) alkylene group,
  —CO$_2$R$_7$ wherein R$_7$ represents a linear or branched (C$_1$–C$_6$)alkyl group, an aryl group, a cycloalkyl group, a heterocycle, an —R$_6$-aryl group, an —R$_6$-cycloalkyl group or an —R$_6$-heterocycle wherein R$_6$ is as defined hereinbefore,
  —COR$_8$ wherein R$_8$ represents a hydrogen atom, a linear or branched (C$_1$–C$_6$)alkyl group, an aryl group, a cycloalkyl group, a heterocycle, an —R$_6$-aryl group, an —R$_6$-cycloalkyl group or an —R$_6$-heterocycle wherein R$_6$ is as defined hereinbefore, and
  —CONH—R$_8$ wherein R$_8$ is as defined hereinbefore,
or R$_1$ does not exist when the nitrogen atom carrying it is already carrying an intracyclic double bond, R$_2$ represents a group selected from
  cyano,
  —CO$_2$R$_8$ wherein R$_8$ is as defined hereinbefore,
  —CONHR$_8$ wherein R$_8$ is as defined hereinbefore,
  mono(C$_1$–C$_6$)alkylamino(C$_1$–C$_6$)alkylaminocarbonyl, di(C$_1$–C$_6$)alkylamino-(C$_1$–C$_6$)-alkylaminocarbonyl, the alkyl moieties of each of which groups may be linear or branched,
  —NR$_8$R$_9$ wherein R$_8$ is as defined hereinbefore and R$_9$ represents a group as defined for R$_8$,
  —NH—CO$_2$R$_7$ wherein R$_7$ is as defined hereinbefore, and
  —COR$_8$ wherein R$_8$ is as defined hereinbefore, R$_3$ and R$_4$ together form a (C$_3$–C$_{10}$)cycloalkyl group, R$_5$ represents a hydrogen atom, a linear or branched (C$_1$–C$_6$)alkyl group or an aryl-(C$_1$–C$_6$)alkyl group in which the alkyl moiety may be linear or branched, Ra, Rb, Rc and Rd, which may be identical or different, each represents, independently of the others, a group selected from hydrogen, halogen, linear or branched (C$_1$–C$_6$)alkyl, hydroxy, linear or branched (C$_1$–C$_6$) alkoxy, linear or branched trihalo-(C$_1$–C$_6$)alkyl, linear or branched trihalo-(C$_1$–C$_6$)alkoxy, nitro, cyano, amino, linear or branched (C$_1$–C$_6$)alkylamino, di(C$_1$–C$_6$)alkylamino in which each alkyl moiety may be linear or branched, aryl, aryl-(C$_1$–C$_6$)alkyl in which the alkyl moiety may be linear or branched, carboxy, linear or branched (C$_1$–C$_6$)alkylcarbonyloxy, linear or branched (C$_1$–C$_6$)acyl, aryloxy and aryl-(C$_1$–C$_6$) alkoxy in which the alkoxy moiety may be linear or branched, to their isomers, and also to addition salts thereof with a pharmaceutically acceptable acid or base, it being understood that:

"cycloalkyl" is to be understood as a mono- or bi-cyclic group that is saturated (or optionally contains one or more unsaturations that do not confer an aromatic character to the ring system), contains from 3 to 10 carbon atoms, and is optionally substituted by one or more identical or different groups selected from halogen, hydroxy, linear or branched $(C_1-C_6)$alkyl and linear or branched $(C_1-C_6)$alkoxy, "aryl" is to be understood as a phenyl, naphthyl, tetrahydronaphthyl, dihydronaphthyl, indenyl or indanyl group, each of those groups being optionally substituted by one or more identical or different groups selected from halogen, hydroxy, cyano, nitro, linear or branched $(C_1-C_6)$alkyl, linear or branched $(C_1-C_6)$alkoxy, amino, linear or branched $(C_1-C_6)$ alkylamino, di$(C_1-C_6)$alkylamino in which each of the alkyl moieties may be linear or branched, aryloxy, aryl-$(C_1-C_6)$alkoxy which the alkoxy moiety may be linear or branched, linear or branched trihalo$(C_1-C_6)$alkyl, linear or branched $(C_1-C_6)$acyl, linear or branched $(C_1-C_6)$alkoxycarbonyl, linear or branched $(C_1-C_6)$alkylaminocarbonyl and oxo, "heterocycle" is to be understood as a saturated or unsaturated, mono- or bi-cyclic group of aromatic or non-aromatic character having from 5 to 12 ring members and containing one, two or three hetero atom, identical or different, hetero atoms selected from oxygen, nitrogen and sulphur, it being understood that the heterocycle may be optionally substituted by one or more identical or different groups selected from halogen, hydroxy, linear or branched $(C_1-C_6)$alkyl, linear or branched $(C_1-C_6)$alkoxy, nitro, oxo, and amino (optionally substituted by one or two linear or branched $(C_1-C_6)$alkyl groups).

Among the heterocycles there may be mentioned, by way of indication and without implying any limitation, the groups pyridinyl, thienyl, furyl, imidazolyl, 4H-pyranyl-4-one, pyrazinyl, pyrimidinyl, isoxazolyl, tetrazolyl, pyrrolyl, pyrazolyl, quinolyl, isoquinolyl, quinazolinyl, pyrrolidinyl, piperidyl, piperazinyl, 1,2,3-thiadiazolyl, . . . .

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned, without implying any limitation, sodium hydroxide, potassium hydroxide, triethylamine, tert-butylamine, etc.

According to an advantageous variant, preferred compounds of the invention are those wherein $R_3$ and $R_4$ together form a saturated monocyclic $(C_3-C_{10})$cycloalkyl group optionally substituted by one or more groups as defined hereinbefore. Especially advantageously, $R_3$ and $R_4$ together form an unsubstituted saturated monocyclic $(C_4-C_6)$cycloalkyl group. Even more especially, $R_3$ and $R_4$ together form a cyclobutyl group.

The substituents $R_1$ preferred in accordance with the invention are the hydrogen atom and the group $—COR_8$ wherein $R_8$ is as defined for formula (I). According to an advantageous variant, the preferred substituent $R_1$ is the group $—COR_{8a}$ wherein $R_{8a}$ represents an aryl group or a heterocycle.

The substituent $R_2$ preferred in accordance with the invention is the group $—CO_2R_8$ wherein $R_8$ is as defined for formula (I). According to an advantageous variant, the preferred substituent $R_2$ is the group $—CO_2R_{8b}$ wherein $R_{8b}$ represents a linear or branched $(C_1-C_6)$alkyl group or cycloalkyl. Especially advantageously, $R_{8b}$ represents an ethyl or cyclopentyl group.

The substituent $R_5$ preferred in accordance with the invention is the hydrogen atom.

According to an especially advantageous variant, preferred compounds of the invention are the 2,3,4,9-tetrahydro-1H-β-carboline compounds of formula (I'):

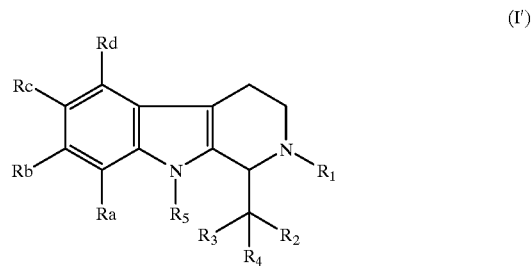

(I')

wherein:

$R_1$, $R_2$, $R_3$, $R_4$, $R_5$, Ra, Rb, Rc and Rd are as defined for formula (I).

Compounds preferred in accordance with the invention are:

cyclopentyl 1-(6-chloro-2,3,4,9-tetrahydro-1H-β-carbolin-1-yl)cyclobutanecarboxylate, ethyl 1-(6-bromo-2,3,4,9-tetrahydro-1H-β-carbolin-1-yl) cyclobutanecarboxylate, ethyl 1-[6-chloro-2-(1H-imidazol-5-ylcarbonyl)-2,3,4,9-tetrahydro-1H-β-carbolin-1-yl] cyclobutanecarboxylate, ethyl 1-(6-methyl-2,3,4,9-tetrahydro-1H-β-carbolin-1-yl) cyclobutanecarboxylate, ethyl 1-(5,6-dichloro-2,3,4,9-tetrahydro-1H-β-carbolin-1-yl)cyclobutanecarboxylate, ethyl 1-(6-chloro-2,3,4,9-tetrahydro-1H-β-carbolin-1-yl) cyclobutanecarboxylate, ethyl 1-(6,7-dichloro-2,3,4,9-tetrahydro-1H-β-carbolin-1-yl)cyclobutanecarboxylate, and ethyl 1-(6-methoxy-2,3,4,9-tetrahydro-1H-β-carbolin-1-yl)cyclobutanecarboxylate.

The isomers, and also the addition salts with a pharmaceutically acceptable acid or base, of the preferred compounds form an integral part of the invention.

The invention extends also to a process for the preparation of the compounds of formula (I) which is characterised in that there is used as starting material a compound of formula (II):

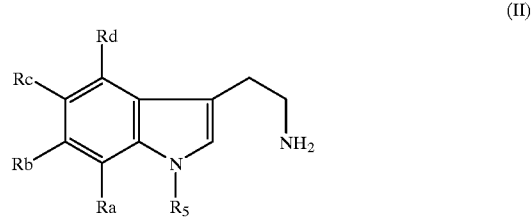

(II)

wherein Ra, Rb, Rc, Rd and $R_5$ are as defined for formula (I), which compound of formula (II) is reacted, in accordance with synthesis conditions of the type used for peptide coupling, with a compound of formula (III):

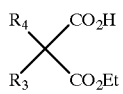
(III)

wherein $R_3$ and $R_4$ are as defined for formula (I), to yield a compound of formula (IV):

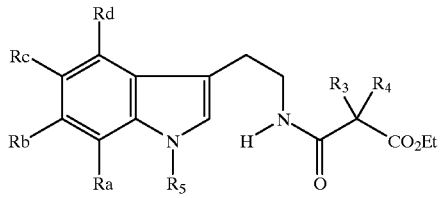
(IV)

wherein Ra, Rb, Rc, Rd, $R_3$, $R_4$ and $R_5$ are as defined hereinbefore, which compounds of formula (IV) are treated in the presence of phosphorus oxychloride in a solvent, such as toluene or benzene, to yield the compounds of formula (I/a), a particular case of the compounds of formula (I):

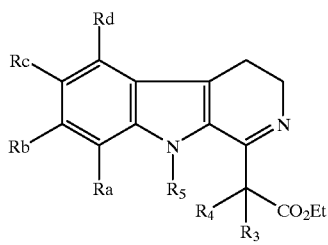
(I/a)

wherein Ra, Rb, Rc, Rd, $R_3$, $R_4$ and $R_5$ are as defined hereinbefore, which compounds of formula (I/a) are:
  either reduced according to the conditions conventional in organic synthesis to yield the compounds of formula (I/b), a particular case of the compounds of formula (I):

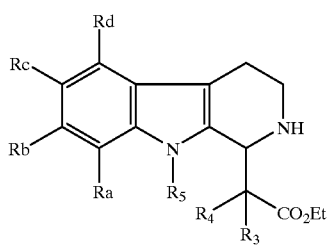
(I/b)

wherein Ra, Rb, Rc, Rd, $R_3$, $R_4$ and $R_5$ are as defined hereinbefore, which compounds of formula (I/b) are treated under basic conditions in the presence of a compound of formula (V):

$R_1$—X  (V)

wherein $R_1$ is as defined for formula (I) and X represents a leaving group customarily used in organic synthesis, to yield the compounds of formula (I/c), a particular case of the compounds of formula (I):

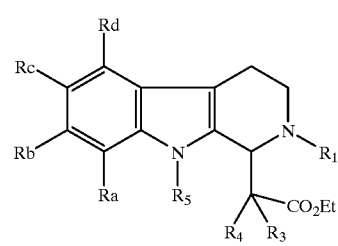
(I/c)

or subjected to the action of oxidising agents customarily used in organic synthesis to yield the compounds of formula (I/d), a particular case of the compounds of formula (I):

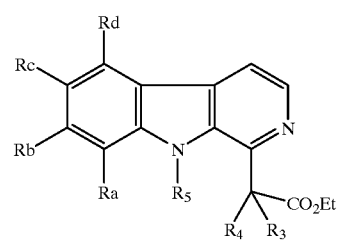
(I/d)

wherein Ra, Rb, Rc, Rd, $R_3$, $R_4$ and $R_5$ are as defined hereinbefore, the totality of the compounds of formula (I/a), (I/b), (I/c) and (I/d) constituting the compounds of formula (I/e), a particular case of the compounds of formula (I):

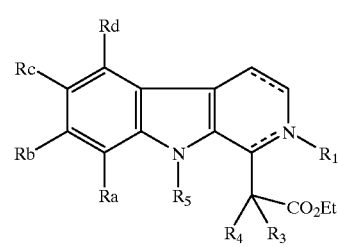
(I/e)

wherein Ra, Rb, Rc, Rd, $R_1$, $R_3$, $R_4$ and $R_5$ are as defined for formula (I), which compound of formula (I/e),
  is subjected to the conditions of transesterification in the presence of a Lewis acid and of a compound of formula (VI):

$R_7$—OH  (VI)

wherein $R_7$ is as defined for formula (I), to yield the compounds of formula (1/f), a particular case of the compounds of formula (I):

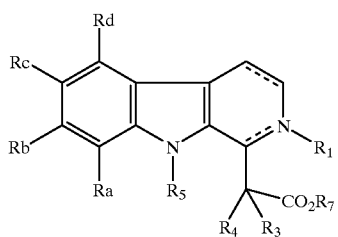

(I/f)

wherein Ra, Rb, Rc, Rd, $R_1$, $R_3$, $R_4$, $R_5$ and $R_7$ are as defined hereinbefore, or is hydrolysed under basic conditions to yield the compounds of formula (I/g), a particular case of the compounds of formula (I):

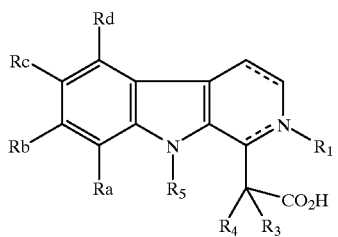

(I/g)

wherein Ra, Rb, Rc, Rd, $R_1$, $R_3$, $R_4$ and $R_5$ are as defined hereinbefore, which compound of formula (I/g):

is treated according to conventional amidation conditions with a compound of formula (VII):

 (VII)

$R_8$—$NH_2$ wherein $R_8$ is as defined for formula (I), to yield the compounds of formula (I/h), a particular case of the compounds of formula (I):

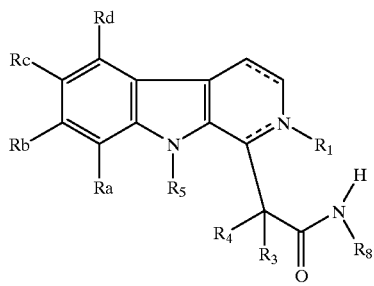

(I/h)

wherein Ra, Rb, Rc, Rd, $R_1$, $R_3$, $R_4$, $R_5$ and $R_8$ are as defined hereinbefore, the primary amide function of which compounds of formula (I/h), in the particular case where $R_8$ represents a hydrogen atom, is converted into a nitrile function according to the conditions conventional in organic synthesis to yield the compounds of formula (I/i), a particular case of the compounds of formula (I):

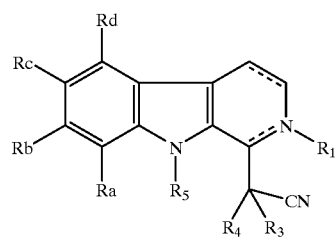

(I/i)

wherein Ra, Rb, Rc, Rd, $R_1$, $R_3$, $R_4$ and $R_5$ are as defined hereinbefore, or the carboxylic acid function of which compound of formula (I/g) is converted into an aldehyde, by a reaction sequence comprising reduction then oxidation according to the conditions customary in organic chemistry, to yield the compounds of formula (I/j), a particular case of the compounds of formula (I):

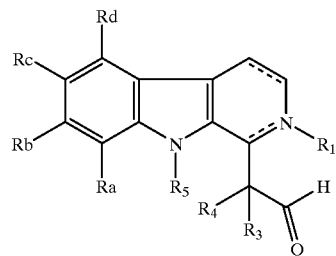

(I/j)

wherein Ra, Rb, Rc, Rd, $R_1$, $R_3$, $R_4$ and $R_5$ are as defined hereinbefore, which compound of formula (I/j) is placed in the presence of a compound of formula (VIII):

$R_7$—M—X (VIII)

wherein $R_7$ is as defined for formula (I), M represents a metal atom, such as an alkali metal atom or a magnesium atom, and X represents a leaving group, such as a halogen atom, to yield as intermediates the compounds of formula (IX):

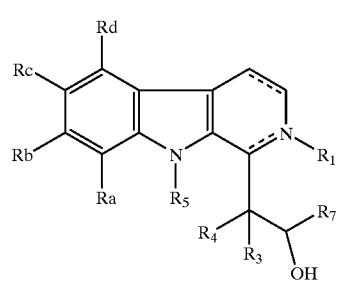

(IX)

wherein Ra, Rb, Rc, Rd, $R_1$, $R_3$, $R_4$, $R_5$ and $R_7$ are as defined hereinbefore, which compounds of formula (IX) are oxidised by means of an oxidising agent commonly used in organic synthesis, to yield the compounds of formula (I/k), a particular case of the compounds of formula (I):

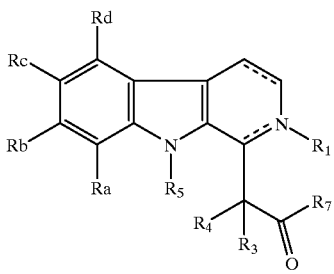

(I/k)

wherein Ra, Rb, Rc, Rd, $R_1$, $R_3$, $R_4$, $R_5$ and $R_7$ are as defined hereinbefore, or is treated with diphenylphosphoryl azide, in the presence of triethylamine and a compound of formula $R_7$—OH (VI) as defined hereinbefore, to yield the compounds of formula (I/l), a particular case of the compounds of formula (I):

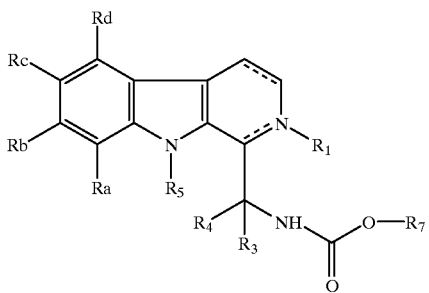

(I/l)

wherein Ra, Rb, Rc, Rd, $R_1$, $R_3$, $R_4$, $R_5$ and $R_7$ are as defined hereinbefore, which compounds of formula (I/l), in the particular case where $R_7$ represents a benzyl group, are subjected to hydrogenolysis conditions in the presence of palladium-on-carbon to yield the compounds of formula (I/m), a particular case of the compounds of formula (I):

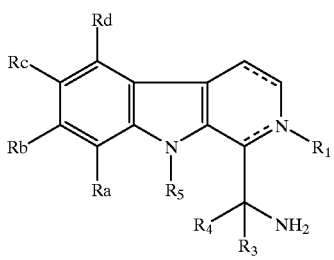

(I/m)

the primary amine function of which compounds of formula (I/m) is converted into a secondary or tertiary amine function, according to conventional methods, to yield the compounds of formula (I/n), a particular case of the compounds of formula (I):

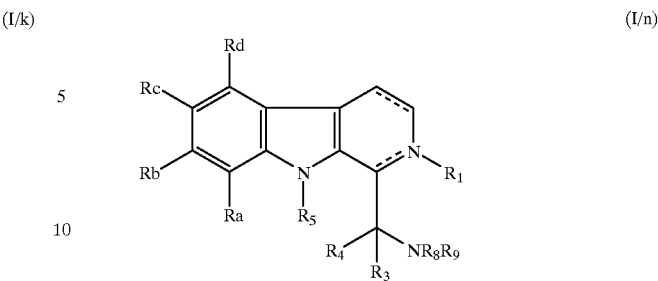

(I/n)

wherein Ra, Rb, Rc, Rd, $R_1$, $R_3$, $R_4$, $R_5$, $R_8$ and $R_9$ are as defined for formula (I), it being understood that in that case $R_8$ and $R_9$ do not simultaneously represent a hydrogen atom, the compounds (I/a) to (I/n) constituting the totality of the compounds of the invention, which compounds are purified, if necessary, according to a conventional purification technique, may be separated, if desired, into their different isomers according to a conventional separation technique, and are optionally converted into addition salts with a pharmaceutically acceptable acid or base.

The compounds of formulae (II), (III), (V), (VI), (VII) and (VIII) are either commercially available compounds or are compounds obtained according to known methods of organic synthesis.

The present invention relates also to pharmaceutical compositions comprising as active ingredient at least one compound of formula (I), an optical isomer thereof or an addition salt thereof with a pharmaceutically acceptable acid or base, alone or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous), per- or trans-cutaneous, nasal, rectal, perlingual, ocular or respiratory administration, and especially tablets or dragees, sublingual tablets, sachets, gelatin capsules, lozenges, suppositories, creams, ointments, dermal gels, injectable or drinkable preparations, aerosols, eye or nose drops, etc.

The compounds of the invention have a strong serotonergic $5HT_{2B}/5HT_{2C}$ activity and particularly $5\text{-}HT_{2C}$ antagonist activity (demonstrated in the binding test, where the compounds of the invention have in particular a $K_i$ of from $10^{-7}$ to $10^{-9}$ nM for that receptor). The pharmaceutical compositions containing at least one compound of formula (I) are consequently useful in the treatment of depression, psychosis, schizophrenia, phobia, anxiety, panic attacks, sleep disorders, appetite disorders, impulsive and aggressive disorders, sexual disorders and migraine.

The useful dosage varies in accordance with the age and weight of the patient, the administration route, the nature and the severity of the disorder, and the administration of any other treatments, and ranges from 0.1 mg to 500 mg per day taken in one or more administrations.

The following Examples illustrate the invention but do not limit it in any way.

The starting materials and/or the reagents used are known products or products prepared according to known procedures.

The structures of the compounds described in the Examples and the synthesis steps were determined according to conventional spectrophotometric techniques (infrared, NMR, mass spectrometry, . . . ).

EXAMPLE 1

Ethyl 1-(6-chloro-2,3,4,9-tetrahydro-1H-β-carbolin-1-yl)cyclobutanecarboxylate Hydrochloride Step A: Ethyl 1-({[2-(5-chloro-1H-indol-3-yl)ethyl]amino}carbonyl)cyclobutanecarboxylate 23.1 g of 5-chlorotryptamine hydrochloride, 17.3 g of monoethyl cyclobutanedicarboxylate, 36 ml of diisopropylethylamine and 33.7 g of O-(benzotriazol-1-yl)-N,N,N',N'-tetramethyluronium tetrafluoroborate are stirred for 20 hours at ambient temperature in 200 ml of dichloromethane. After washing with water, drying over sodium sulphate and filtering off the organic phase over Celite, evaporation under reduced pressure enables the expected product to be isolated.

Step B: Ethyl 1-(6-chloro-2,3,4,9-tetrahydro-1H-β-carbolin-1-yl)cyclobutanecarboxylate Hydrochloride 32 g of the product obtained in Step A are heated at reflux in a solution of 400 ml of toluene and 35 ml of $POCl_3$. After 3 hours, the reaction mixture is concentrated under reduced pressure, the residue is taken up in 300 ml of ethanol, and 5 g of sodium borohydride are slowly added. After 30 minutes, 300 ml of water are added and the ethanol is distilled off. After extraction of the residue with dichloromethane, drying and evaporation under reduced pressure, the oily residue obtained is converted into the hydrochloride in an ethanolic hydrogen chloride solution. The expected product is isolated by filtration and drying in vacuo.

Melting point: 158–160° C.; Elemental microanalysis:

|  | C | H | N | Cl |
|---|---|---|---|---|
| % calculated | 58.54 | 6.00 | 7.59 | 19.20 |
| % found | 58.33 | 5.97 | 7.61 | 19.60 |

EXAMPLE 2

Ethyl (R,S)-1-(6-bromo-2,3,4,9-tetrahydro-1H-β-carbolin-1-yl)cyclobutanecarboxylate Hydrochloride The procedure is as in Example 1, using as substrate in Step A 5-bromotryptamine hydrochloride.

Melting point: 246–247° C.; Elemental microanalysis:

|  | C | H | N |
|---|---|---|---|
| % calculated | 52.25 | 5.36 | 6.77 |
| % found | 52.14 | 5.41 | 6.61 |

EXAMPLE 3

(+)-Ethyl 1-(6-bromo-2,3,4,9-tetrahydro-1H-β-carbolin-1-yl)cyclobutanecarboxylate and its Hydrochloride The product of Example 2 is subjected to chiral phase chromatography (Chiralcel AD), the mobile phase being composed of a 1000/1 ethanol/diethylamine mixture. The compound is eluted having an enantiomeric excess of 98% and is then converted into the hydrochloride by the action of ethereal hydrogen chloride.

Melting point: 226–227° C.; $[\alpha]_D^{21°\,C.}=+23.26°$.

EXAMPLE 4

(−)-Ethyl 1-(6-bromo-2,3,4,9-tetrahydro-1H-β-carbolin-1-yl)cyclobutanecarboxylate and its Hydrochloride The other product separated during the chromatography carried out in Example 3 corresponds to the expected product, with an enantiomeric excess of 95%, and this is then converted into its hydrochloride.

Melting point: 226–227° C.; $[\alpha]_D^{21°\,C.}=-23.18°$.

EXAMPLE 5

Ethyl 1-(6-methyl-2,3,4,9-tetrahydro-1H-β-carbolin-1-yl)cyclobutanecarboxylate Hydrochloride The procedure is as in Example 1, using as substrate in Step A 5-methyltryptamine hydrochloride.

Melting point: 235–237° C.; Elemental microanalysis:

|  | C | H | N | Cl |
|---|---|---|---|---|
| % calculated | 65.41 | 7.22 | 8.03 | 10.16 |
| % found | 65.27 | 7.29 | 7.88 | 10.46 |

EXAMPLE 6

Ethyl 1-(6,7-dichloro-2,3,4,9-tetrahydro-1H-β-carbolin-1-yl)cyclobutanecarboxylate Hydrochloride The procedure is as in Example 1, using as substrate in Step A 5,6-dichlorotryptamine hydrochloride.

Melting point: >260° C.; Elemental microanalysis:

|  | C | H | N | Cl |
|---|---|---|---|---|
| % calculated | 53.55 | 5.24 | 6.94 | 26.34 |
| % found | 53.88 | 4.99 | 6.83 | 26.10 |

EXAMPLE 7

Ethyl 1-(6-methoxy-2,3,4,9-tetrahydro-1H-β-carbolin-1-yl)cyclobutanecarboxylate Hydrochloride The procedure is as in Example 1, using as substrate in Step A 5-methoxytryptamine hydrochloride.

Melting point: 190–192° C.; Elemental microanalysis:

|  | C | H | N | Cl |
|---|---|---|---|---|
| % calculated | 62.55 | 6.91 | 7.68 | 9.72 |
| % found | 62.07 | 7.10 | 7.47 | 9.82 |

EXAMPLE 8

Ethyl 1-(2,3,4,9-tetrahydro-1H-β-carbolin-1-yl)cyclobutanecarboxylate Hydrochloride The procedure is as in Example 1, using as substrate in Step A tryptamine hydrochloride.

Melting point: 204–206° C.; Elemental microanalysis:

|  | C | H | N | Cl |
|---|---|---|---|---|
| % calculated | 64.57 | 6.92 | 8.37 | 10.59 |
| % found | 64.60 | 6.98 | 8.25 | 10.66 |

EXAMPLE 9

Ethyl 1-(6,7-dimethoxy-2,3,4,9-tetrahydro-1H-β-carbolin-1-yl)cyclobutanecarboxylate Hydrochloride The procedure is as in Example 1, using as substrate in Step A 5,6-dimethoxytryptamine hydrochloride.

Melting point: 169–170° C.; Elemental microanalysis:

|  | C | H | N | Cl |
|---|---|---|---|---|
| % calculated | 60.83 | 6.89 | 7.09 | 8.98 |
| % found | 60.22 | 7.00 | 7.05 | 8.66 |

EXAMPLE 10

Ethyl 1-(6,7-dibromo-2,3,4,9-tetrahydro-1H-β-carbolin-1-yl)cyclobutanecarboxylate Hydrochloride The procedure is as in Example 1, using as substrate in Step A 5,6-dibromotryptamine hydrochloride.

Melting point: >260° C.; Elemental microanalysis:

|  | C | H | N | Cl | Br |
|---|---|---|---|---|---|
| % calculated | 43.89 | 4.30 | 5.69 | 7.20 | 32.44 |
| % found | 44.00 | 4.31 | 5.67 | 7.29 | 32.00 |

EXAMPLE 11

Ethyl 1-(6-phenyl-2,3,4,9-tetrahydro-1H-β-carbolin-1-yl)cyclobutanecarboxylate Hydrochloride 2 g of the compound obtained in Example 2, 1 g of phenylboronic acid, 1.7 g of cesium fluoride, 3.2 g of cesium bromide and 0.7 g of tetrakis(triphenylphosphine)palladium (0) are heated at reflux for 20 hours in 200 ml of dimethoxyethane, then purified on silica gel (dichloromethane/methanol: 97/3) to yield the expected compound after conversion into a salt using a solution of ethereal hydrogen chloride.

Melting point: >260° C.; Elemental microanalysis:

|  | C | H | N | Cl |
|---|---|---|---|---|
| % calculated | 69.31 | 6.67 | 6.74 | 8.53 |
| % found | 68.70 | 6.45 | 6.65 | 8.27 |

EXAMPLE 12

Ethyl 1-(7-trifluoromethyl-2,3,4,9-tetrahydro-1H-β-carbolin-1-yl)cyclobutanecarboxylate Hydrochloride The procedure is as in Example 1, using as substrate in Step A 6-trifluoromethyltryptamine.

Melting point: 241° C.; Elemental microanalysis:

|  | C | H | N | Cl |
|---|---|---|---|---|
| % calculated | 56.65 | 5.50 | 6.95 | 8.80 |
| % found | 56.68 | 5.29 | 6.82 | 9.10 |

EXAMPLE 13

Ethyl 1-(6-tert-butyl-2,3,4,9-tetrahydro-1H-β-carbolin-1-yl)cyclobutanecarboxylate Hydrochloride The procedure is as in Example 1, using as substrate in Step A 5-tert-butyltryptamine hydrochloride.

Melting point: lyophilisate; Elemental microanalysis:

|  | C | H | N | Cl |
|---|---|---|---|---|
| % calculated | 64.68 | 8.12 | 6.86 | 8.68 |
| % found | 64.20 | 8.16 | 7.07 | 8.90 |

EXAMPLE 14

Ethyl 1-(7-methyl-2,3,4,9-tetrahydro-1H-β-carbolin-1-yl)cyclobutanecarboxylate Hydrochloride The procedure is as in Example 1, using as substrate in Step A 6-methyltryptamine hydrochloride.

Melting point: 236° C.; Elemental microanalysis:

|  | C | H | N | Cl |
|---|---|---|---|---|
| % calculated | 64.49 | 7.60 | 7.92 | 10.02 |
| % found | 64.05 | 7.86 | 7.73 | 10.20 |

EXAMPLE 15

Ethyl 1-(6-hydroxy-2,3,4,9-tetrahydro-1H-β-carbolin-1-yl)cyclobutanecarboxylate 12 ml of 1M boron tribromide in dicloromethane are added at −30° C., under an inert atmosphere, to a solution of 2 g of the compound obtained in Example 7 in 50 ml of dichloromethane. After reaction for two hours at ambient temperature, the reaction mixture is hydrolysed with 1 ml of a saturated ammonium chloride solution. The precipitate obtained is filtered off, washed with water and then dried, enabling the expected product to be isolated.

Melting point: 215–216° C.; Elemental microanalysis:

|  | C | H | N |
|---|---|---|---|
| % calculated | 68.77 | 7.05 | 8.91 |
| % found | 67.56 | 6.88 | 8.77 |

EXAMPLE 16

Ethyl 1-(7-chloro-6-fluoro-2,3,4,9-tetrahydro-1H-β-carbolin-1-yl)cyclobutanecarboxylate Hydrochloride The procedure is as in Example 1, using as substrate in Step A 5-fluoro-6-chlorotryptarmine.

Melting point: 251–252° C.; Elemental microanalysis:

|  | C | H | N | Cl |
|---|---|---|---|---|
| % calculated | 58.54 | 6.00 | 7.59 | 19.20 |
| % found | 58.33 | 5.97 | 7.61 | 19.60 |

EXAMPLE 17

Ethyl 1-(6-fluoro-2,3,4,9-tetrahydro-1H-β-carbolin-1-yl)cyclobutanecarboxylate Hydrochloride The procedure is as in Example 1, using as substrate in Step A 5-fluorotryptamine.

Melting point: 212–213° C.; Elemental microanalysis:

|  | C | H | N | Cl |
|---|---|---|---|---|
| % calculated | 61.27 | 6.28 | 7.94 | 10.05 |
| % found | 61.25 | 6.28 | 7.91 | 10.38 |

EXAMPLE 18

Ethyl 1-(5,6-dichloro-2,3,4,9-tetrahydro-1H-β-carbolin-1-yl)cylobutanecarboxylate Hydrochloride The procedure is as in Example 1, using as substrate in Step A 4,5-dichlorotryptamine hydrochloride.

Melting point: 242–243° C.; Elemental microanalysis:

|  | C | H | N | Cl |
|---|---|---|---|---|
| % calculated | 53.58 | 5.33 | 6.87 | 26.07 |
| % found | 53.49 | 5.41 | 6.72 | 26.59 |

EXAMPLE 19

Ethyl 1-(5,6-dibromo-2,3,4,9-tetrahydro-1H-β-carbolin-1-yl)cyclobutanecarboxylate Hydrochloride The procedure is as in Example 1, using as substrate in Step A 4,5-dibromotryptamine hydrochloride.

Melting point: 183–184° C.; Elemental microanalysis:

|  | C | H | N | Cl | Br |
|---|---|---|---|---|---|
| % calculated | 43.89 | 4.30 | 5.69 | 7.20 | 32.44 |
| % found | 44.20 | 4.40 | 5.69 | 7.30 | 32.00 |

EXAMPLE 20

Ethyl 1-(6-chloro-9-methyl-2,3,4,9-tetrahydro-1H-β-carbolin-1yl)cyclobutanecarboxylate Hydrochloride The procedure is as in Example 1, using as substrate in Step A 5-chloro-1-methyltryptamine hydrochloride.

Melting point: >260° C.; Elemental microanalysis:

|  | C | H | N | Cl |
|---|---|---|---|---|
| % calculated | 59.54 | 6.31 | 7.31 | 18.50 |
| % found | 59.80 | 6.39 | 7.09 | 18.38 |

EXAMPLE 21

Ethyl 1-(6-chloro-9-ethyl-2,3,4,9-tetrahydro-1H-β-carbolin-1-yl)cyclobutanecarboxylate Hydrochloride The procedure is as in Example 1, using as substrate in Step A 5-chloro-1-ethyltryptamine.

Melting point: 231–232° C.; Elemental microanalysis:

|  | C | H | N | Cl |
|---|---|---|---|---|
| % calculated | 60.46 | 6.60 | 7.05 | 17.84 |
| % found | 60.48 | 6.73 | 7.02 | 18.11 |

EXAMPLE 22

Ethyl 1-(6-methoxy-9-methyl-2,3,4,9-tetrahydro-1H-β-carbolin-1-yl)cyclobutanecarboxylate Hydrochloride The procedure is as in Example 1, using as substrate in Step A 5-methoxy-1-methyltryptamine hydrochloride.

Melting point: >250° C.; Elemental microanalysis:

|  | C | H | N | Cl |
|---|---|---|---|---|
| % calculated | 63.40 | 7.18 | 7.39 | 9.36 |
| % found | 62.96 | 7.62 | 7.17 | 9.06 |

EXAMPLE 23

Cyclopentyl 1-(6-chloro-2,3,4,9-tetrahydro-1H-β-carbolin-1-yl)cyclobutanecarboxylate Hydrochloride 4.0 g of the compound of Example 1 are heated at the reflux of 80 ml of cyclopentanol in the presence of 1 ml of titanium tetraisopropoxide. After reaction for 24 hours, the reaction mixture is diluted with water and then filtered. After extraction with dichloromethane, drying and evaporation under reduced pressure, crystallisation of the residue from an ethanol-diethyl ether-hydrogen chloride mixture enables the expected product to be isolated.

Melting point: 208–209° C.; Elemental microanalysis:

|  | C | H | N | Cl |
|---|---|---|---|---|
| % calculated | 61.62 | 6.40 | 6.84 | 17.32 |
| % found | 61.42 | 6.50 | 6.65 | 17.17 |

EXAMPLE 24

Isopropyl 1-(6-chloro-2,3,4,9-tetrahydro-1H-β-carbolin-1-yl)cyclobutanecarboxylate Hydrochloride The procedure is as in Example 23, using isopropanol as reagent instead of cyclopentanol.

Melting point: 244–245° C.; Elemental microanalysis:

|  | C | H | N | Cl |
|---|---|---|---|---|
| % calculated | 59.54 | 6.31 | 7.31 | 18.50 |
| % found | 59.57 | 6.29 | 7.19 | 18.72 |

EXAMPLE 25

Benzyl 1-(6-methoxy-2,3,4,9-tetrahydro-1H-β-carbolin-1-yl)cyclobutanecarboxylate Hydrochloride The procedure is as in Example 23, using as substrate the product of Example 7 and as reagent benzyl alcohol.

Melting point: 228–230° C.; Elemental microanalysis:

|  | C | H | N | Cl |
|---|---|---|---|---|
| % calculated | 67.52 | 6.37 | 6.56 | 8.30 |
| % found | 67.96 | 6.49 | 6.64 | 8.77 |

EXAMPLE 26

Methyl 1-(6-chloro-2,3,4,9-tetrahydro-1H-β-carbolin-1-yl)cyclobutanecarboxylate Hydrochloride The procedure is as in Example 23, using methanol as reagent.

Melting point: 232–233° C.; Elemental microanalysis:

|  | C | H | N | Cl |
|---|---|---|---|---|
| % calculated | 57.07 | 5.71 | 7.83 | 19.82 |
| % found | 56.99 | 5.54 | 7.50 | 20.27 |

EXAMPLE 27

Methyl 1-(6-methoxy-2,3,4,9-tetrahydro-1H-β-carbolin-1-yl)cyclobutanecarboxylate Hydrochloride The procedure is as in Example 23, starting from the compound of Example 7 and the reagent of Example 26.

Melting point: 208–209° C.; Elemental microanalysis:

|  | C | H | N | Cl |
|---|---|---|---|---|
| % calculated | 61.62 | 6.61 | 7.98 | 10.11 |
| % found | 61.56 | 6.61 | 7.88 | 10.23 |

EXAMPLE 28

Ethyl 1-(6-chloro-2,3,4,9-tetraydro-1H-β-carbolin-1-yl)cyclohexanecarboxylate Hydrochloride The procedure is as in Example 1, using as reagent monoethyl cyclohexanedicarboxylate.

Melting point: 245–246° C.; Elemental microanalysis:

|  | C | H | N | Cl |
|---|---|---|---|---|
| % calculated | 60.46 | 6.60 | 7.05 | 17.84 |
| % found | 60.30 | 6.52 | 7.01 | 18.24 |

EXAMPLE 29

Ethyl 1-(6-chloro-2,3,4,9-tetrahydro-1H-β-carbolin-1-yl)cyclopentanecarboxylate Hydrochloride The procedure is as in Example 1, using as reagent monomethyl cyclopentanedicarboxylate.

Melting point: 231–232° C.; Elemental microanalysis:

|  | C | H | N | Cl |
|---|---|---|---|---|
| % calculated | 59.54 | 6.31 | 7.31 | 18.50 |
| % found | 59.63 | 6.32 | 7.08 | 18.63 |

EXAMPLE 30

Ethyl 1-(6-chloro-9-methyl-2,3,4,9-tetrahydro-1H-β-carbolin-1-yl)cyclopentanecarboxylate Hydrochloride The procedure is as in Example 20, using as reagent in Step A the reagent used in Example 29.

Melting point: 113–115° C.; Elemental microanalysis:

|  | C | H | N | Cl |
|---|---|---|---|---|
| % calculated | 66.56 | 6.98 | 7.76 | 9.82 |
| % found | 66.23 | 7.16 | 7.49 | 10.28 |

EXAMPLE 31

Ethyl 1-(6-methoxy-2,3,4,9-tetrahydro-1H-β-carbolin-1-yl)cyclopentanecarboxylate Hydrochloride The procedure is as in Example 7, using as reagent in Step A the reagent used in Example 29.

Melting point: 175–176° C.; Elemental microanalysis:

|  | C | H | N | Cl |
|---|---|---|---|---|
| % calculated | 63.02 | 7.21 | 7.34 | 9.30 |
| % found | 62.72 | 7.43 | 7.17 | 9.14 |

EXAMPLE 32

1-(6-Chloro-2,3,4,9-tetrahydro-1H-β-carbolin-1-yl)cyclobutanecarboxylic Acid

A suspension of 1 g of the compound of Example 1 in 15 ml of water, 30 ml of ethanol and 5 ml of 1 M sodium hydroxide solution is heated at 50° C. for 10 hours. The reaction mixture is then cooled and 5 ml of 1M HCl are added. The resulting precipitate is suction-filtered off, washed with water and then dried in vacuo, enabling the expected product to be isolated.

Melting point: >275° C.; Elemental microanalysis:

|  | C | H | N | Cl |
|---|---|---|---|---|
| % calculated | 63.05 | 5.62 | 9.19 | 11.63 |
| % found | 62.22 | 5.67 | 9.20 | 11.75 |

EXAMPLE 33

1-(6-Chloro-9-methyl-2,3,4,9-tetrahydro-1H-β-carbolin-1-yl)cyclobutanecarboxylic Acid The procedure is as in Example 32, using as substrate the compound obtained in Example 20.

Melting point: >260° C.; Elemental microanalysis:

|  | C | H | N | Cl |
|---|---|---|---|---|
| % calculated | 64.05 | 6.01 | 8.79 | 11.12 |
| % found | 64.08 | 5.95 | 8.67 | 11.35 |

EXAMPLE 34

1-(6-Chloro-2,3,4,9-tetrahydro-1H-β-carbolin-1-yl)cyclopentanecarboxylic Acid

The procedure is as in Example 32, using as substrate the compound obtained in Example 29.

Melting point: >260° C.; Elemental microanalysis:

|  | C | H | N | Cl |
|---|---|---|---|---|
| % calculated | 64.05 | 6.01 | 8.79 | 11.12 |
| % found | 64.45 | 6.13 | 8.66 | 11.50 |

EXAMPLE 35

1-(2,3,4,9-Tetrahydro-1H-β-carbolin-1-yl)cyclobutanecarboxylic Acid

The procedure is as in Example 32, using as substrate the compound obtained in Example 8.

Melting point: 280–281° C.; Elemental microanalysis:

|  | C | H | N |
|---|---|---|---|
| % calculated | 71.09 | 6.71 | 10.36 |
| % found | 71.11 | 6.88 | 10.22 |

EXAMPLE 36

1-(6-Methoxy-2,3,4,9-tetrahydro-1H-β-carbolin-1-yl)cyclobutanecarboxylic Acid

The procedure is as in Example 32, using as substrate the compound obtained in Example 7.

Melting point: >260° C.; Elemental microanalysis:

|  | C | H | N |
|---|---|---|---|
| % calculated | 67.98 | 6.71 | 9.33 |
| % found | 67.96 | 7.03 | 8.96 |

EXAMPLE 37

1-(6-Methyl-2,3,4,9-tetrahydro-1H-β-carbolin-1-yl)cyclobutanecarboxylic Acid

The procedure is as in Example 32, using as substrate the compound of Example 5.

Melting point: >250° C.; Elemental microanalysis:

|  | C | H | N |
|---|---|---|---|
| % calculated | 71.37 | 7.11 | 9.79 |
| % found | 70.98 | 7.15 | 9.58 |

EXAMPLE 38

1-(7-Methyl-2,3,4,9-tetrahydro-1H-β-carbolin-1-yl)cyclobutanecarboxylic Acid

The procedure is as in Example 32, using as substrate the compound of Example 14.

Melting point: >260° C. Elemental microanalysis:

|  | C | H | N |
|---|---|---|---|
| % calculated | 69.58 | 6.98 | 9.54 |
| % found | 70.10 | 7.10 | 9.54 |

EXAMPLE 39

1-(6-Tert-butyl-2,3,4,9-tetrahydro-1H-β-carbolin-1-yl)cyclobutanecarboxylic Acid The procedure is as in Example 32, using as substrate the compound of Example 13.

Melting point: >260° C.; Elemental microanalysis:

|  | C | H | N |
|---|---|---|---|
| % calculated | 70.13 | 8.27 | 8.18 |
| % found | 70.67 | 7.98 | 8.29 |

EXAMPLE 40

1-(7-Trifluoromethyl-2,3,4,9-tetrahydro-1H-β-carbolin-1-yl)cyclobutanecarboxylic Acid The procedure is as in Example 32, using as substrate the compound of Example 12.

Melting point: >260° C.; Elemental microanalysis:

|  | C | H | N |
|---|---|---|---|
| % calculated | 57.33 | 5.36 | 7.87 |
| % found | 58.28 | 5.56 | 7.86 |

EXAMPLE 41

Ethyl 1-(6-chloro-2-methyl-2,3,4,9-tetrahydro-1H-β-carbolin-1-yl)cyclobutanecarboxylate Hydrochloride 0.3 ml of methyl iodide and 0.8 g of $NaHCO_3$ are added to a solution of 1 g of the compound of Example 1 in 25 ml of ethanol. After reaction for 24 hours at ambient temperature, the reaction mixture is concentrated under reduced pressure and then the residue is taken up in a mixture of water and dichloromethane. After extraction, drying and filtration, the organic phase is concentrated under reduced pressure. Crystallisation from a solution of ethanol and ethereal hydrogen chloride enables the expected product to be obtained.

Melting point: 170–171° C.; Elemental microanalysis:

|  | C | H | N | Cl |
|---|---|---|---|---|
| % calculated | 59.54 | 6.31 | 7.31 | 18.50 |
| % found | 59.28 | 6.24 | 7.12 | 18.42 |

EXAMPLE 42

Ethyl 1-(6-chloro-2,9-dimethyl-2,3,4,9-tetrahydro-1H-β-carbolin-1-yl)cyclobutanecarboxylate Hydrochloride The procedure is as in Example 41, using as substrate the compound of Example 20.

Melting point: 238–240° C.; Elemental microanalysis:

|  | C | H | N | Cl |
|---|---|---|---|---|
| % calculated | 60.46 | 6.60 | 7.05 | 17.84 |
| % found | 60.49 | 6.57 | 6.90 | 18.25 |

EXAMPLE 43

Ethyl 1-(6-chloro-2-methyl-2,3,4,9-tetrahydro-1H-β-carbolin-1-yl)cyclopentanecarboxylate The procedure is as in Example 41, using as substrate the compound of Example 29.

Melting point: 145–146° C.; Elemental microanalysis:

|  | C | H | N | Cl |
|---|---|---|---|---|
| % calculated | 59.54 | 6.31 | 7.31 | 18.50 |
| % found | 59.28 | 6.24 | 7.12 | 18.42 |

EXAMPLE 44

Ethyl 1-(6-chloro-2,9-dimethyl-2,3,4,9-tetrahydro-1H-β-carbolin-1-yl)cyclopentanecarboxylate The procedure is as in Example 41, using as substrate the compound of Example 30.

Melting point: 109° C.; Elemental microanalysis:

|  | C | H | N | Cl |
|---|---|---|---|---|
| % calculated | 67.28 | 7.26 | 7.47 | 9.46 |
| % found | 67.26 | 7.46 | 7.56 | 10.19 |

EXAMPLE 45

Ethyl 1-(6-chloro-2-methyl-2,3,4,9-tetrahydro-1H-β-carbolin-1-yl)cyclohexanecarboxylate Hydrochloride The procedure is as in Example 41, using as substrate the compound of Example 28.

Melting point: 1 78–185° C.; Elemental microanalysis:

|  | C | H | N | Cl |
|---|---|---|---|---|
| % calculated | 61.31 | 6.86 | 6.81 | 17.24 |
| % found | 61.36 | 6.77 | 6.71 | 16.89 |

EXAMPLE 46

Ethyl 1-(2-methyl-2,3,4,9-tetrahydro-1H-β-carbolin-1-yl)cyclobutanecarboxylate

The procedure is as in Example 41, using as substrate the compound of Example 8.

Melting point: 142–144° C.; Elemental microanalysis:

|  | C | H | N |
|---|---|---|---|
| % calculated | 73.05 | 7.74 | 8.97 |
| % found | 72.66 | 7.75 | 8.79 |

EXAMPLE 47

Ethyl 1-(6-methoxy-2-methyl-2,3,4,9-tetrahydro-1H-β-carbolin-1-yl)cyclobutanecarboxylate The procedure is as in Example 41, using as substrate the compound of Example 7.

Melting point: 124–125° C.; Elemental microanalysis:

|  | C | H | N |
|---|---|---|---|
| % calculated | 70.15 | 7.65 | 8.18 |
| % found | 70.16 | 7.64 | 8.00 |

EXAMPLE 48

Ethyl 1-(6-methoxy-2-methyl-2,3,4,9-tetrahydro-1H-β-carbolin-1-yl)cyclopentanecarboxylate The procedure is as in Example 41, using as substrate the compound of Example 31.

Melting point: 113–114° C.; Elemental microanalysis:

|  | C | H | N |
|---|---|---|---|
| % calculated | 70.76 | 7.92 | 7.86 |
| % found | 70.21 | 7.85 | 7.75 |

EXAMPLE 49

Ethyl 1-(2-benzyl-6-chloro-2,3,4,9-tetrahydro-1H-β-carbolin-1-yl)cyclobutanecarboxylate The procedure is as in Example 41, using benzyl bromide as reagent instead of methyl iodide.

|            | C     | H    | N    | Cl   |
|------------|-------|------|------|------|
| % calculated | 70.99 | 6.43 | 6.62 | 8.38 |
| % found      | 70.95 | 6.51 | 6.79 | 9.08 |

EXAMPLE 50

1-(6-Chloro-2-methyl-2,3,4,9-tetrahydro-1H-β-carbolin-1-yl)cyclobutanecarboxylic Acid The procedure is as in Example 32, using as substrate the compound of Example 41.

Melting point: 174–175° C.; Elemental microanalysis:

|            | C     | H    | N    | Cl    |
|------------|-------|------|------|-------|
| % calculated | 64.05 | 6.01 | 8.79 | 11.12 |
| % found      | 63.97 | 5.95 | 8.59 | 11.45 |

EXAMPLE 51

1-(6-Chloro-2,9-dimethyl-2,3,4,9-tetrahydro-1H-β-carbolin-2-yl)cyclobutanecarboxylic Acid The procedure is as in Example 32, using as substrate the compound of Example 42.

Melting point: >260° C.; Elemental microanalysis:

|            | C     | H    | N    | Cl    |
|------------|-------|------|------|-------|
| % calculated | 64.96 | 6.36 | 8.42 | 10.65 |
| % found      | 64.40 | 6.40 | 8.18 | 10.91 |

EXAMPLE 52

1-(6-Chloro-2-methyl-2,3,4,9-tetrahydro-1H-β-carbolin-1-yl)cyclopentanecarboxylic Acid The procedure is as in Example 32, using as substrate the compound of Example 43.

Melting point: 171–173° C.; Elemental microanalysis:

|            | C     | H    | N    | Cl    |
|------------|-------|------|------|-------|
| % calculated | 64.96 | 6.36 | 8.42 | 10.65 |
| % found      | 64.59 | 6.39 | 8.21 | 10.77 |

EXAMPLE 53

1-(6-Chloro-2,9-dimethyl-2,3,4,9-tetrahydro-1H-β-carbolin-1-yl)cyclopentanecarboxylic Acid The procedure is as in Example 32, using as substrate the compound of Example 44.

Melting point: 197–198° C.; Elemental microanalysis:

|            | C     | H    | N    | Cl   |
|------------|-------|------|------|------|
| % calculated | 62.54 | 6.91 | 7.68 | 9.71 |
| % found      | 62.83 | 7.07 | 7.64 | 9.99 |

EXAMPLE 54

1-(6-Chloro-2-benzyl-2,3,4,9-tetrahydro-1H-β-carbolin-1-yl)cyclobutanecarboxylic Acid The procedure is as in Example 32, using as substrate the compound of Example 49.

Melting point: 178–180° C.; Elemental microanalysis:

|            | C     | H    | N    | Cl   |
|------------|-------|------|------|------|
| % calculated | 68.00 | 6.01 | 6.89 | 8.72 |
| % found      | 67.81 | 6.04 | 6.91 | 9.30 |

EXAMPLE 55

Ethyl 1-[6chloro-2-(1H-imidazol-5-ylcarbonyl)-2,3,4,9-tetrahydro-1H-β-carbolin-1-yl]cyclobutanecarboxylate Hydrochloride 1.84 g of the compound of Example 1, 1.8 g of N-tritylimidazole-4-carboxylic acid, 1.92 ml of diisopropylethylamine and 1.76 g of O-(benzotriazol-1-yl)-N,N,N',N'-tetramethyluronium tetrafluoroborate are stirred at ambient temperature for 24 hours. After dilution with 500 ml of water, filtration, and extraction with dichloromethane, the organic phases are dried and filtered and then concentrated under reduced pressure. Crystallisation of the residue in an ethanol-diethyl ether-hydrogen chloride mixture enables the expected compound to be isolated.

Melting point: 170–171° C.

EXAMPLE 56

Ethyl 1-(2-benzoyl-6-chloro-2,3,4,9-tetrahydro-1H-β-carbolin-1-yl)cyclobutanecarboxylate The procedure is as in Example 55, using benzoyl chloride as reagent instead of N-tritylimidazole-4-carboxylic acid.

Melting point: 195–196° C.; Elemental microanalysis:

|            | C     | H    | N    | Cl   |
|------------|-------|------|------|------|
| % calculated | 68.72 | 5.77 | 6.41 | 8.11 |
| % found      | 68.36 | 5.80 | 6.26 | 8.07 |

EXAMPLE 57

Ethyl 1-[6-chloro-2-(2-thienylcarbonyl)-2,3,4,9-tetrahydro-1H-β-carbolin-1-yl]cyclobutanecarboxylate The procedure is as in Example 55, using as reagent 2-thiophenoyl chloride.

Melting point: 190–191° C.; Elemental microanalysis:

|  | C | H | N | Cl | S |
|---|---|---|---|---|---|
| % calculated | 62.36 | 5.23 | 6.32 | 7.24 | 8.00 |
| % found | 62.43 | 5.29 | 6.30 | 7.17 | 7.98 |

EXAMPLE 58

Ethyl 1-[6-chloro-2-(3-furoyl)-2,3,4,9-tetrahydro-1H-β-carbolin-1-yl]cyclobutanecarboxylate The procedure is as in Example 55, using as reagent 3-furoyl chloride.

Melting point: 176–177° C.

EXAMPLE 59

Ethyl 1-[6-chloro-2-(4-chlorobenzoyl)-2,3,4,9-tetrahydro-1H-β-carbolin-1-yl]cyclobutanecarboxylate The procedure is as in Example 55, using as reagent 4-chlorobenzoyl chloride.

Melting point: 204–205° C.; Elemental microanalysis:

|  | C | H | N | Cl |
|---|---|---|---|---|
| % calculated | 63.70 | 5.13 | 5.94 | 15.04 |
| % found | 63.78 | 5.27 | 5.95 | 14.69 |

EXAMPLE 60

Ethyl 1-[6-chloro-2-(4-methoxybenzoyl)-2,3,4,9-tetrahydro-1H-β-carbolin-1-yl]cyclobutanecarboxylate The procedure is as in Example 55, using as reagent 4-methoxybenzoyl chloride.

Melting point: 169–170° C.; Elemental microanalysis:

|  | C | H | N | Cl |
|---|---|---|---|---|
| % calculated | 66.88 | 5.83 | 6.00 | 7.59 |
| % found | 66.92 | 5.92 | 6.02 | 7.55 |

EXAMPLE 61

Ethyl 1-[6-bromo-2-(3-furoyl)-2,3,4,9-tetrahydro-1H-β-carbolin-1-yl]cyclobutanecarboxylate The procedure is as in Example 55, using as substrate the compound of Example 2 and as reagent 3-furoyl chloride.

Melting point: 178–179° C.; Elemental microanalysis:

|  | C | H | N | Br |
|---|---|---|---|---|
| % calculated | 58.61 | 4,92 | 5.94 | 16.95 |
| % found | 58.61 | 5.11 | 5.77 | 16.92 |

EXAMPLE 62

Ethyl 1-[6-chloro-2-(2-pyridinylcarbonyl)-2,3,4,9-tetrahydro-1H-β-carbolin-1-yl]cyclobutanecarboxylate The procedure is as in Example 55, using as reagent 2-pyridinecarboxylic acid.

Melting point: 166–167° C.; Elemental microanalysis:

|  | C | H | N | Cl |
|---|---|---|---|---|
| % calculated | 65.83 | 5.52 | 9.60 | 8.10 |
| % found | 65.71 | 5.67 | 9.58 | 8.29 |

EXAMPLE 63

Ethyl 1-{6-chloro-2-[4-oxo-4H-pyran-2-yl)carbonyl]-2,3,4,9-tetrahydro-1H-β-carbolin-1-yl}cyclobutanecarboxylate The procedure is as in Example 55, using as reagent 4-oxo-4H-pyrane-3-carboxylic acid.

Melting point: 153–154° C.; Elemental microanalysis:

|  | C | H | N | Cl |
|---|---|---|---|---|
| % calculated | 63.37 | 5.10 | 6.16 | 7.79 |
| % found | 63.38 | 5.17 | 6.08 | 7.96 |

EXAMPLE 64

Ethyl 1-[6-chloro-2-(3-pyridinylcarbonyl)-2,3,4,9-tetrahydro-1H-β-carbolin-1-yl]cyclobutanecarboxylate The procedure is as in Example 55, using as reagent 3-pyridinecarboxylic acid.

Melting point: 184–185° C.; Elemental microanalysis:

|  | C | H | N | Cl |
|---|---|---|---|---|
| % calculated | 65.83 | 5.52 | 9.60 | 8.10 |
| % found | 65.91 | 5.61 | 9.53 | 8.10 |

EXAMPLE 65

Ethyl 1-[6-chloro-2-(2-pyrazinylcarbonyl)-2,3,4,9-tetrahydro-1H-β-carbolin-1-yl]cyclobutanecarboxylate The procedure is as in Example 55, using as reagent 2-pyrazinylcarboxylic acid.

Melting point: 167–168° C.; Elemental microanalysis:

|  | C | H | N | Cl |
|---|---|---|---|---|
| % calculated | 62.94 | 5.28 | 12.76 | 8.08 |
| % found | 63.04 | 5.40 | 12.86 | 8.03 |

EXAMPLE 66

Ethyl 1-[6-chloro-2-(2-pyrimidinylcarbonyl)-2,3,4,9-tetradydro-1H-β-carbolin-1-yl]cyclobutanecarboxylate The procedure is as in Example 55, using as reagent 2-pyrimidinylcarboxylic acid.

Melting point: 158–160° C.; Elemental microanalysis:

|  | C | H | N | Cl |
|---|---|---|---|---|
| % calculated | 62.94 | 5.28 | 12.76 | 8.08 |
| % found | 62.04 | 5.30 | 12.72 | 8.11 |

EXAMPLE 67

Ethyl 1-[6-chloro-2-(5-isoxazolylcarbonyl)-2,3,4,9-tetrahydro-1H-β-carbolin-1-yl]cyclobutanecarboxylate The procedure is as in Example 55, using as reagent 5-isoxazolylcarboxylic acid. Melting point: 166–167° C.; Elemental microanalysis:

|  | C | H | N | Cl |
|---|---|---|---|---|
| % calculated | 61.76 | 5.18 | 9.82 | 8.29 |
| % found | 61.80 | 5.24 | 9.74 | 8.33 |

EXAMPLE 68

Ethyl 1-[6-chloro-2-(4-pyridinylcarbonyl)-2,3,4,9-tetrahydro-1H-β-carbolin-1-yl]cyclobutanecarboxylate The procedure is as in Example 55, using as reagent 4-pyridinecarboxylic acid.

Melting point: 205–206° C.; Elemental microanalysis:

|  | C | H | N | Cl |
|---|---|---|---|---|
| % calculated | 65.83 | 5.52 | 9.60 | 8.10 |
| % found | 65.85 | 5.52 | 9.53 | 8.07 |

EXAMPLE 69

Ethyl 1-[6-bromo-2-(5-isoxazolylcarbonyl)-2,3,4,9-tetrahydro-1H-β-carbolin-1-yl]cyclobutanecarboxylate The procedure is as in Example 55, using as substrate the compound of Example 2 and as reagent the reagent of Example 67.

Melting point: 170–171° C.; Elemental microanalysis:

|  | C | H | N | Br |
|---|---|---|---|---|
| % calculated | 55.94 | 4.69 | 8.90 | 16.92 |
| % found | 56.02 | 4.73 | 8.72 | 16.67 |

EXAMPLE 70

Ethyl 1-[6-chloro-2-(1H-pyrrol-2-ylcarbonyl)-2,3,4,9-tetrahydro-1H-β-carbolin-1-yl]cyclobutanecarboxylate The procedure is as in Example 55, using as reagent 1H-2-pyrrolecarboxylic acid.

Melting point: 209–210° C.; Elemental microanalysis:

|  | C | H | N | Cl |
|---|---|---|---|---|
| % calculated | 64.86 | 5.68 | 9.87 | 8.32 |
| % found | 64.89 | 5.73 | 9.76 | 8.48 |

EXAMPLE 71

Ethyl 1-{6-chloro-2-[2-(1H-1,2,3,4-tetraazol-1-yl)acetyl]-2,3,4,9-tetrahydro-1H-β-carbolin-1-yl}cyclobutanecarboxylate The procedure is as in Example 55, using as reagent 2-(1H-1,2,3,4-tetraazol-1-yl)acetic acid.

Melting point: 123–124° C.; Elemental microanalysis:

|  | C | H | N | Cl |
|---|---|---|---|---|
| % calculated | 56.95 | 5.23 | 18.97 | 8.00 |
| % found | 57.22 | 5.36 | 17.86 | 7.26 |

EXAMPLE 72

Ethyl 1-{6-chloro-2-[(1-methyl-1H-imidazol4-yl)carbonyl]-2,3,4,9-tetrahydro-1H-β-carbolin-1-yl}cyclobutanecarboxylate The procedure is as in Example 55, using as reagent 1-methyl-1H-imidazole-4-carboxylic acid.

Melting point: 180–181° C.; Elemental microanalysis:

|  | C | H | N | Cl |
|---|---|---|---|---|
| % calculated | 62.65 | 5.71 | 12.71 | 8.04 |
| % found | 63.02 | 5.67 | 12.61 | 8.02 |

EXAMPLE 73

Ethyl (1R)-1-[6-chloro-2-(1H-imidazol-5-ylcarbonyl)-2,3,4,9-tetrahydro-1H-β-carbolin-1-yl]cyclobutanecarboxylate The compound of Example 55 is eluted on a chiral column (CHIRALPAK AD) using ethanol as eluant, enabling the expected product to be isolated having an enantiomeric excess of 98%.

Melting point: 140–142° C.; Elemental microanalysis:

|  | C | H | N | Cl |
|---|---|---|---|---|
| % calculated | 61.90 | 5.43 | 13.12 | 8.30 |
| % found | 61.71 | 5.52 | 12.82 | 9.02 |

EXAMPLE 74

Ethyl (1S)-1-[6-chloro-2-(1H-imidazol-5-ylcarbonyl)-2,3,4,9-tetrahydro-1H-β-carbolin-1-yl]cyclobutanecarboxylate The second compound eluted in the course of the chromatography carried out in Example 73 corresponds to the expected product, having an enantiomeric excess of 98%.

Melting point: 140–142° C.; Elemental microanalysis:

|  | C | H | N | Cl |
|---|---|---|---|---|
| % calculated | 61.90 | 5.43 | 13.12 | 8.30 |
| % found | 61.43 | 5.58 | 12.79 | 8.35 |

EXAMPLE 75

Ethyl 1-{6-chloro-2-[(1-methyl-1H-imidazol-5-yl)carbonyl]-2,3,4,9-tetrahydro-1H-β-carbolin-1-yl}cyclobutanecarboxylate The procedure is as in Example 55, using as reagent 1-methyl-1H-imidazole-5-carboxylic acid.

Melting point: 203–204° C.; Elemental microanalysis:

|  | C | H | N | Cl |
|---|---|---|---|---|
| % calculated | 62.65 | 5.71 | 12.71 | 8.04 |
| % found | 62.71 | 5.74 | 12.73 | 8.19 |

EXAMPLE 76

Ethyl 1-{6-chloro-2-[(5-methyl-1H-imidazol4-yl)carbonyl]-2,3,4,9-tetrahydro-1H-β-carbolin-1-yl}cyclobutanecarboxylate The procedure is as in Example 55, using as reagent 5-methyl-1H-imidazole-4-carboxylic acid.

Melting point: 161–162° C. Elemental microanalysis:

|  | C | H | N | Cl |
|---|---|---|---|---|
| % calculated | 62.65 | 5.71 | 12.71 | 8.04 |
| % found | 63.18 | 6.21 | 11.93 | 7.52 |

EXAMPLE 77

Ethyl 1- {6-chloro-2-[(4-methyl-1,2,3-thiadiazol-5-yl)carbonyl]-2,3,4,9-tetrahydro-1H-β-carbolin-1-yl}cyclobutanecarboxylate The procedure is as in Example 55, using as reagent 4-methyl-1,2,3-thiadiazole-5-carboxylic acid.

Melting point: 162–163° C.; Elemental microanalysis:

|  | C | H | N | Cl | S |
|---|---|---|---|---|---|
| % calculated | 57.57 | 5.05 | 12.21 | 7.72 | 6.99 |
| % found | 57.49 | 5.05 | 12.05 | 8.04 | 6.93 |

EXAMPLE 78

Ethyl 1-[6-chloro-2-(1,2,3-thiadiazol-4-ylcarbonyl)-2,3,4,9-tetrahydro-1H-β-carbolin-1-yl]cyclobutanecarboxylate The procedure is as in Example 55, using as reagent 1,2,3-thiadiazole-4-carboxylic acid.

Melting point: 224–225° C.; Elemental microanalysis:

|  | C | H | N | Cl | S |
|---|---|---|---|---|---|
| % calculated | 56.69 | 4.76 | 12.59 | 7.97 | 7.21 |
| % found | 56.90 | 4.96 | 12.28 | 8.00 | 7.13 |

EXAMPLE 79

Ethyl 1-(2-acetyl-6-chloro-2,3,4,9-tetrahydro-1H-β-carbolin-1-yl)cyclobutanecarboxylate The procedure is as in Example 55, using as reagent acetyl chloride.

Melting point: 218–219° C.; Elemental microanalysis:

|  | C | H | N | Cl |
|---|---|---|---|---|
| % calculated | 64.08 | 6.18 | 7.47 | 9.46 |
| % found | 64.06 | 6.30 | 7.34 | 9.45 |

EXAMPLE 80

Ethyl 1-(2-acetyl-6-methoxy-2,3,4,9-tetrahydro-1H-β-carbolin-1-yl)cyclobutanecarboxylate The procedure is as in Example 55, using as substrate the compound of Example 7 and as reagent the reagent used in Example 79.

Melting point: 180–182° C.; Elemental microanalysis:

|  | C | H | N |
|---|---|---|---|
| % calculated | 68.09 | 7.07 | 7.56 |
| % found | 68.18 | 7.28 | 7.56 |

EXAMPLE 81

Ethyl 1-[6-methoxy-2-(2-furoyl)-2,3,4,9-tetrahydro-1H-β-carbolin-1-yl]cyclobutanecarboxylate The procedure is as in Example 55, using as substrate the compound of Example 7 and as reagent 2-furoyl chloride.

Melting point: 149–150° C.; Elemental microanalysis:

|  | C | H | N |
|---|---|---|---|
| % calculated | 68.23 | 6.20 | 6.63 |
| % found | 68.21 | 6.35 | 6.66 |

EXAMPLE 82

Ethyl 1-[6-chloro-2-(2-furoyl)-2,3,4,9-tetrahydro-1H-β-carbolin-1-yl]cyclobutanecarboxylate The procedure is as in Example 55, using as reagent 2-furoyl chloride.

Melting point: 195–196° C.; Elemental microanalysis:

|  | C | H | N | Cl |
|---|---|---|---|---|
| % calculated | 64.71 | 5.43 | 6.56 | 8.30 |
| % found | 64.61 | 5.55 | 6.54 | 8.29 |

EXAMPLE 83

1-(2-Acetyl-6-chloro-2,3,4,9-tetrahydro-1H-β-carbolin-1-yl)cyclobutanecarboxylic Acid The procedure is as in Example 55, using as substrate the compound of Example 32 and as reagent acetyl chloride.

Melting point: >250° C.; Elemental microanalysis:

|  | C | H | N | Cl |
|---|---|---|---|---|
| % calculated | 62.34 | 5.52 | 8.08 | 10.22 |
| % found | 62.12 | 5.69 | 8.01 | 10.25 |

EXAMPLE 84

1-(2-Acetyl-2,3,4,9-tetrahydro-1H-β-carbolin-1-yl)cyclobutanecarboxylic Acid

The procedure is as in Example 55, using as substrate the compound of Example 35 and as reagent acetyl chloride.

Melting point: 244–246° C.; Elemental microanalysis:

|  | C | H | N |
|---|---|---|---|
| % calculated | 69.21 | 6.45 | 8.97 |
| % found | 69.03 | 6.70 | 8.69 |

EXAMPLE 85

1-(6-Chloro-2,3,4,9-tetrahydro-1H-β-carbolin-1-yl)cyclobutanecarboxamide Hydrochloride 0.8 g of tert-butyl pyrocarbonate is added at 0° C. to a solution of 1 g of the compound of Example 1 in 20 ml of dioxane, 20 ml of water and 10 ml of 1M sodium hydroxide solution. After reaction for 4 hours, the reaction mixture is diluted by the addition of water and acidified with a 5% citric acid solution. After extraction with ethyl acetate, drying the organic phases, and concentration under reduced pressure, the residue obtained is diluted with 50 ml of tetrahydrofuran and 0.5 ml of N-methylmorpholine. After cooling the mixture to −10° C., 0.3 ml of ethyl chloroformate are added, followed by 0.2 ml of a 28% ammonium hydroxide solution. After reaction for 12 hours, the solvent is distilled off. The residue is then taken up in a water/dichloromethane mixture. After decanting, drying and concentrating under reduced pressure, the residue is treated with a solution of ethanol and ethereal hydrogen chloride, enabling the desired product to be obtained in the form of the hydrochloride.

Melting point: 229–230° C.; Elemental microanalysis:

|  | C | H | N | Cl |
|---|---|---|---|---|
| % calculated | 56.48 | 5.63 | 12.35 | 20.84 |
| % found | 56.30 | 5.65 | 12.07 | 20.81 |

EXAMPLE 86

Tert-butyl 1-[1-(aminocarbonyl)cyclobutyl]-6-chloro-1,3,4,9-tetrahydro-2H-β-carboline-2-carboxylate The product is a co-product obtained in the synthesis of the compound of Example 85.

Melting point: 229–230° C.; Elemental microanalysis:

|  | C | H | N | Cl |
|---|---|---|---|---|
| % calculated | 62.45 | 6.49 | 10.40 | 8.78 |
| % found | 62.53 | 6.53 | 10.12 | 8.80 |

EXAMPLE 87

Ethyl 1-[1-(aminocarbonyl)cyclobutyl]-6-chloro-1,3,4,9-tetrahydro-2H-β-carboline-2-carboxylate 0.3 ml of ethyl chloroformate, and then 0.2 ml of a 28% ammonium hydroxide solution, are added at −10° C. to a solution of 1 g of the compound of Example 32 in 50 ml of tetrahydrofuran and 0.5 ml of N-methylmorpholine. After reaction for 12 hours, the solvent is distilled off; the residue is then taken up in a water/dichloromethane mixture. The expected product is isolated by decanting, drying and concentrating under reduced pressure.

Melting point: 200–20° C.; Elemental microanalysis:

|  | C | H | N | Cl |
|---|---|---|---|---|
| % calculated | 60.72 | 5.90 | 11.18 | 9.43 |
| % found | 60.49 | 6.00 | 10.82 | 9.29 |

EXAMPLE 88

1-(6-Chloro-2-methyl-2,3,4,9-tetrahydro-1H-β-carbolin-1-yl)cyclobutanecarboxamide The procedure is as in Example 87, using as substrate the compound of Example 33.

Melting point: 129–130° C.; Elemental microanalysis:

|  | C | H | N | Cl |
|---|---|---|---|---|
| % calculated | 64.25 | 6.34 | 13.22 | 11.16 |
| % found | 64.03 | 6.43 | 12.47 | 11.09 |

EXAMPLE 89

1-(6-Chloro-2-methyl-2,3,4,9-tetrahydro-1H-β-carbolin-1-yl)cyclohexanecarboxamide Hydrochloride The procedure is as in Example 87, using as substrate the compound of Example 45.

EXAMPLE 90

1-(2-Methyl-2,3,4,9-tetrahydro-1H-β-carbolin-1-yl)
cyclobutanecarboxamide

The procedure is as in Example 87, using as substrate the compound of Example 46 and as reagent aminocarbaldehyde.

Melting point: 145–146° C.

EXAMPLE 91

1-(2-Formyl-6-chloro-2,3,4,9-tetrahydro-1H-β-carbolin-1-yl)cyclobutanecarboxamide Reaction between the compound of Example 1 and aminocarbaldehyde in the presence of sodium methoxide in dimethylformamide enables the desired product to be obtained.

Melting point: >260° C.; Elemental microanalysis:

|  | C | H | N | Cl |
|---|---|---|---|---|
| % calculated | 61.54 | 5.47 | 12.66 | 10.68 |
| % found | 61.36 | 5.61 | 12.26 | 10.75 |

EXAMPLE 92

1-(6-Chloro-2,3,4,9-tetrahydro-1H-β-carbolin-1-yl)-
N-[2-(dimethylamino)ethyl]cyclobutanecarboxamide
Dihydrochloride The procedure is as in Example 85, using 2-(N,N-dimethylamino)ethylamine as reagent instead of ammonium hydroxide.

Melting point: 229–231° C.; Elemental microanalysis:

|  | C | H | N | Cl |
|---|---|---|---|---|
| % calculated | 53.64 | 6.53 | 12.51 | 23.75 |
| % found | 53.13 | 6.39 | 12.31 | 24.35 |

EXAMPLE 93

Tert-butyl 6-chloro-1-[1-({[2-(dimethylamino)ethyl]
amino}carbonyl)cyclobutyl]-1,3,4,9-tetrahydro-2H-
β-carboline-2-carboxylate The product is obtained as co-product in the synthesis of the compound of Example 92.

Melting point: 84–85° C.; Elemental microanalysis:

|  | C | H | N | Cl |
|---|---|---|---|---|
| % calculated | 63.21 | 7.43 | 11.79 | 7.46 |
| % found | 62.72 | 7.18 | 11.63 | 7.52 |

EXAMPLE 94

1-[2-(Tert-butoxycarbonyl)-6-methyl-2,3,4,9-
tetrahydro-1H-β-carbolin-1-yl]
cyclobutanecarboxylic Acid 5.52 g of tert-butyl pyrocarbonate are added to a solution of 6.5 g of the compound obtained in Example 37 in 50 ml of dioxane and 25 ml of 1M sodium hydroxide solution. After reaction for 20 hours at ambient temperature, 50 ml of ethyl acetate and 100 ml of water are added, and then the reaction mixture is acidified to pH 2.3 using a solution of KHSO₄. The precipitate formed is filtered off, washed with water and dried, enabling the expected product to be isolated.

Melting point: 217–218° C.; Elemental microanalysis:

|  | C | H | N |
|---|---|---|---|
| % calculated | 68.73 | 7.34 | 7.29 |
| % found | 68.42 | 7.28 | 7.18 |

EXAMPLE 95

N-[2(Dimethylamino)ethyl]-1-(6-methoxy-2-methyl-
2,3,4,9-tetrahydro-1H-β-carbolin-1-yl)
cyclobutanecarboxamide The product is obtained by heat treatment of the compound of Example 47 in the presence of a large excess of N,N-(dimethylamino)ethylamine.

Melting point: 187–188° C.; Elemental microanalysis:

|  | C | H | N |
|---|---|---|---|
| % calculated | 68.72 | 8.39 | 14.57 |
| % found | 68.48 | 8.31 | 14.52 |

EXAMPLE 96

Ethyl 1-{6-chloro-2-[(3-pyridinylamino)carbonyl]-2,
3,4,9-tetrahydro-1H-β-carbolin-1-
yl}cyclobutanecarboxylate 0.9 g of 3-pyridylcarbonyl azide in 60 ml of toluene are heated at reflux for 1 hour 30 minutes under an inert atmosphere. After the mixture has returned to ambient temperature, 1.65 g of the compound obtained in Example 1 diluted with 60 ml of dichloromethane are added. The reaction mixture is stirred for 20 hours at ambient temperature, and then the precipitate formed is filtered off, washed and subsequently dried, enabling the expected product to be isolated.

Melting point: 126–128° C.

EXAMPLE 97

Tert-butyl 1-(1-{[(Benzyloxy)carbonyl]
amino}cyclobutyl)-6-methyl-1,3,4,9-tetrahydro-2H-
β-carboline Carboxylate 2.8 g of the compound obtained in Example 94 in 3.3 ml of diphenylphosphoryl azide, 2.1 ml of triethylamine and 5.2 ml of benzyl alcohol are heated to reflux. After working up, chromatography on silica gel (dichloromethane/methanol) enables the expected product to be isolated.

Melting point: 219–220° C.; Elemental microanalysis:

|  | C | H | N |
|---|---|---|---|
| % calculated | 71.14 | 7.20 | 8.58 |
| % found | 70.38 | 7.17 | 8.16 |

EXAMPLE 98

1-(6-Methyl-2,3,4,9-tetrahydro-1H-β-carbolin-1-yl) cyclobutanamine Hydrochloride Step A1: Phenyl 1-(6methyl-2,3,4,9-tetrahydro-1H-β-carbolin-1-yl)cyclobutylcarbamate 0.9 g of the compound obtained in Example 97 are dissolved in 50 ml of ethyl acetate into which gaseous hydrogen chloride is bubbled. After reaction for one hour, the precipitate formed is filtered off, washed with diethyl ether and dried, enabling the expected product to be isolated.

Melting point: 244–245° C.

Step B1: 1-(6Methyl-2,3,4,9-tetrahydro-1H-β-carbolin-1-yl)cyclobutanamine Hydrochloride 0.5 g of the compound obtained in Step A1 are hydrogenated by the action of hydrogen in the presence of 10% palladium-on-carbon in 50 ml of ethanol. After filtration and concentration under reduced pressure, the residue is crystallised from diethyl ether, enabling the expected product to be isolated.

Melting point: 180° C.

EXAMPLE 99

1-(6-Tert-butyl-2,3,4,9-tetrahydro-1H-β-carbolin-1-yl)cyclobutanamine Hydrochloride The procedure is as in Example 94, in Example 97 and then 98 Steps A1 and B1, using as substrate the compound of Example 39.

Melting point: 245° C.; Elemental microanalysis:

|  | C | H | N | Cl |
|---|---|---|---|---|
| % calculated | 66.35 | 8.45 | 12.58 | 10.62 |
| % found | 66.80 | 8.37 | 11.96 | 9.91 |

EXAMPLE 100

Ethyl 1-(6-chloro-4,9-dihydro-3H-β-carbolin-1-yl) cyclobutanecarboxylate

The product is obtained in accordance with the protocol described in Example 1, without the last stage of reduction by the action of sodium borohydride.

Melting point: 141–142° C.; Elemental microanalysis:

|  | C | H | N | Cl |
|---|---|---|---|---|
| % calculated | 65.35 | 5.79 | 8.47 | 10.72 |
| % found | 65.37 | 5.76 | 8.44 | 10.94 |

EXAMPLE 101

Ethyl 1-(6-bromo-4,9-dihydro-3H-β-carbolin-1-yl) cyclobutanecarboxylate

The procedure is as in Example 100, using as substrate the substrate used in Example 2.

Melting point: 132–133° C. Elemental microanalysis:

|  | C | H | N | Br |
|---|---|---|---|---|
| % calculated | 57.61 | 5.10 | 7.46 | 21.29 |
| % found | 57.64 | 5.22 | 7.45 | 21.05 |

EXAMPLE 102

Ethyl 1-(4,9-dihydro-3H-β-carbolin-1-yl) cyclobutanecarboxylate

The procedure is as in Example 100, using as substrate the substrate used in Example 8.

Melting point: 121–122° C.; Elemental microanalysis:

|  | C | H | N |
|---|---|---|---|
| % calculated | 72.95 | 6.80 | 9.45 |
| % found | 72.88 | 6.93 | 9.48 |

EXAMPLE 103

Ethyl 1-(6-methyl-4,9-dihydro-3H-β-carbolin-1-yl) cyclobutanecarboxylate

The procedure is as in Example 100, using as substrate the substrate used in Example 5.

Melting point: 500–103° C.; Elemental microanalysis:

|  | C | H | N |
|---|---|---|---|
| % calculated | 73.52 | 7.14 | 9.03 |
| % found | 73.56 | 7.23 | 8.93 |

EXAMPLE 104

Ethyl 1-(6-methoxy-4,9-dihydro-3H-β-carbolin-1-yl)cyclobutanecarboxylate

The procedure is as in Example 100, using as substrate the substrate used in Example 7.

Melting point: 229–230° C.; Elemental microanalysis:

|  | C | H | N |
|---|---|---|---|
| % calculated | 69.92 | 6.79 | 8.58 |
| % found | 69.51 | 6.63 | 8.33 |

EXAMPLE 105

Ethyl 1-(6-chloro-9-ethyl-4,9-dihydro-3H-β-carbolin-1-yl)cyclobutanecarboxylate

The procedure is as in Example 100, using as substrate the substrate used in Example 21.

Melting point: 115–116° C.; Elemental microanalysis:

|  | C | H | N | Cl |
|---|---|---|---|---|
| % calculated | 66.94 | 6.46 | 7.81 | 9.88 |
| % found | 67.82 | 6.62 | 7.85 | 9.94 |

EXAMPLE 106

Ethyl 1-(6-methoxy-9H-β-carbolin-1-yl)cyclobutanecarboxylate 1.5 g of the compound of Example 104 are refluxed for 96 hours in 10 ml of xylene in the presence of 0.25 g of 10% palladium-on-carbon. After filtration and concentration under reduced pressure, chromatography on silica gel (dichloromethane/ethyl acetate: 80/20) enables the expected product to be isolated.

Melting point: 128–129° C.; Elemental microanalysis:

|  | C | H | N |
|---|---|---|---|
| % calculated | 70.35 | 6.21 | 8.64 |
| % found | 70.36 | 6.22 | 8.63 |

EXAMPLE 107

Ethyl 1-(9H-β-carbolin-1-yl)cyclobutanecarboxylate

The procedure is as in Example 106, using as substrate the compound of Example 102.

Melting point: 144–145° C.; Elemental microanalysis:

|  | C | H | N |
|---|---|---|---|
| % calculated | 73.45 | 6.16 | 9.52 |
| % found | 73.51 | 6.22 | 9.20 |

EXAMPLE 108

Ethyl 1-(6-chloro-9-ethyl-9H-β-carbolin-1-yl)cyclobutanecarboxylate

The procedure is as in Example 106, using as substrate the compound of Example 105.

Melting point: 131–132° C.; Elemental microanalysis:

|  | C | H | N | Cl |
|---|---|---|---|---|
| % calculated | 67.32 | 5.93 | 7.85 | 9.93 |
| % found | 67.19 | 6.08 | 7.57 | 10.12 |

EXAMPLE 109

1-(9H-β-Carbolin-1-yl)cyclobutanecarboxylic Acid

The procedure is as in Example 32, using as substrate the compound of Example 107.

Melting point: 115–116° C.; Elemental microanalysis:

|  | C | H | N |
|---|---|---|---|
| % calculated | 72.17 | 5.30 | 10.52 |
| % found | 71.58 | 5.36 | 10.38 |

EXAMPLE 110

1-(9H-β-Carbolin-1-yl)-N-[2-(dimethylamino)ethyl]cyclobutanecarboxamide Dihydrochloride The product is obtained by heat treatment of the compound of Example 107 in the presence of a large excess of N,N-(dimethylamino)ethylamine.

Melting point: lyophilisate.

EXAMPLE 111

1-(6-Methoxy-9H-β-carbolin-1-yl)-N-[2-(dimethylamino)ethyl]cyclobutanecarboxamide The procedure is as in Example 110, using as substrate the compound of Example 106.

Melting point: lyophilisate.

EXAMPLE 112

1-(6-Hydroxy-9H-β-carbolin-1-yl)-N-[2-(dimethylamino)ethyl]cyclobutanecarboxamide The compound of Example 111 is treated in accordance with the conditions described in Example 15.

Melting point: 182–183° C.

EXAMPLE 113

Ethyl 1-[6-(trifluoromethyl)-2,3,4,9-tetrahydro-1H-β-carbolin-1-yl]-cyclobutanecarboxylate Hydrochloride Step A: 2-[4-(Triethylsilyl)-3-butynyl]-1H-isoindole-1,3(2H)-dione 108 g of (4-triethylsilanylbut-3-yn-1-ol) tosylate in 50 ml of dimethylformamide are added to a suspension of 72.3 g of potassium phthalimidate in 450 ml of dimethylformamide.

After 4 hours at 60° C., the dimethylformamide is distilled off. The residue is taken up in a 1/1 dichloromethane/water mixture, extracted, dried, filtered and then concentrated under reduced pressure, enabling the expected product to be obtained.

Step B: 2-{2-[2-(Triethylslyl)-5-(trifluoromethyl)-1H-indol-3-yl]ethyl}-1H-isoindole-1,3(2H)-dione 5.16 g of 2-iodo-4-trifluoromethylaniline, 11.6 g of the compound obtained in Step A, 0.75 g of dichloropalladium-diphenylphosphine-ferrocene, 0.76 g of lithium chloride and 3.81 g of sodium hydrogen carbonate in 200 ml of dimethylformamide are heated at 100° C. under an inert atmosphere. After 30 hours, the solvent is distilled off. The residue is taken up in a water/dichloromethane mixture, extracted, dried, filtered, and then concentrated under reduced pressure. Chromatography on silica gel (dichloromethane) enables isolation of the expected product, which crystallises in heptane.

Melting point: <25° C.

Step C: 2-[2-(Triethylsilyl)-5-(trifluoromethyl)-1H-indol-3-yl]ethylamine

A mixture of 6.25 g of the compound obtained in Step B and 3.5 ml of hydrazine in 150 ml of ethanol is heated at reflux for one hour, then diluted with 20 ml of 4N HCl and again heated at reflux for one hour. After dilution with 100 ml of water, the ethanol is removed in vacuo. The residue is rendered alkaline by the addition of sodium hydroxide solution and is extracted with dichloromethane. The combined and dried organic fractions are concentrated under reduced pressure, enabling the expected product to be isolated.

Melting point: 56° C.

Step D: 2-[5-(Trifluoromethyl)-1H-indol-3-yl]ethylamine 3.8 g of the compound obtained in Step C are stirred for 72 hours at ambient temperature in 200 ml of tetrahydrofuran and 10 ml of a 1 M solution of tetrabutylammonium fluoride in tetrahydrofuran in the presence of 1 g of 3 Å molecular sieve. After filtering off the resin and evaporating to dryness, the residue is taken up in 100 ml of 1N HCl and washed with dichloromethane. The aqueous phase is then rendered alkaline and extracted with dichloromethane and the combined organic phases are worked up in customary manner. The product obtained crystallises as the hydrochloride in an ethanol-diethyl ether-hydrogen chloride mixture.

Melting point: >250° C.

Step E: Ethyl 1-[6(trifluoromethyl)-2,3,4,9-tetrahydro-1H-β-carbolin-1-yl]cycobutanecarboxylate Hydrochloride The procedure is as in Example 1, using as substrate the product obtained in Step D.

Melting point: 237° C.; Elemental microanalysis:

|  | C | H | N | Cl |
|---|---|---|---|---|
| % calculated | 56.65 | 5.50 | 6.95 | 8.80 |
| % found | 56.62 | 5.60 | 6.92 | 8.90 |

EXAMPLE 114

[1-(6Chloro-2,3,4,9-tetrahydro-1H-β-carbolin-1-yl)cyclobutyl]methanol Hydrochloride 10 g of the compound of Example 1 are dissolved in 400 ml of tetrahydrofuran and 2 g of LiAlH$_4$ are added, in the course of 30 minutes, under an argon atmosphere. After reaction for 3 hours and hydrolysis of the reaction mixture, the mineral salts are suction-filtered off and the filtrate is evaporated to dryness. 7.9 g of product are obtained, which are then converted into the hydrochloride in an ethanol-diethyl ether-hydrogen chloride mixture to yield the expected product.

EXAMPLE 115

1-(6-Chloro-2,3,4,9-tetrahydro-1H-β-carbolin-1-yl)cyclobutanecarbonitrile

Step A: 1-(6-Chloro2,3,4,9-tetrahydro-1H-β-carbolin-1-yl)cyclobutanecarbaldehyde A mixture of 2.8 g of the compound of Example 2 and 3.6 g of Dess-Martin reagent in 100 ml of dichloromethane is stirred for 1 hour at 0° C. After returning to ambient temperature and evaporating off the solvent, chromatography on silica gel (dichloromethane) enables the expected product to be isolated.

Step B: 1-(6-Chloro-2,3,4,9-tetrahydro-1H-β-carbolin-1-yl)-N-hydroxycylobutanecarboxamide A solution of 1.2 g of the compound obtained in Step A in 120 ml of ethanol, 0.54 ml of triethylamine and 0.27 g of hydroxylarnine hydrochloride is stirred for 6 hours and then concentrated under reduced pressure. Chromatography on silica gel (dichloromethane/ethyl acetate: 98/2) enables the expected product to be isolated.

Step C: 1-(6-Chloro-2,3,4,9-tetrahydro-1H-β-carbolin-1-yl)cyclobutanecarbonitrile 0.9 g of the compound obtained in Step B is stirred for 2 hours at ambient temperature in a solution of 10 ml of dioxane, 0.8 ml of pyridine and 0.42 ml of trifluoroacetic anhydride. After evaporating off the solvent, chromatography of the residue on silica gel (dichloromethane/ethyl acetate: 96/4) enables isolation of the expected product, which crystallises in heptane.

Melting point: 218–219° C.; Elemental microanalysis:

|  | C | H | N | Cl |
|---|---|---|---|---|
| % calculated | 67.25 | 5.64 | 14.70 | 12.41 |
| % found | 67.01 | 5.80 | 14.56 | 12.50 |

EXAMPLE 116

1-[1-(6-Chloro-2,3,4,9-tetrahydro-1H-β-carbolin-1-yl)cyclobutyl]-1-propanone Hydrochloride Step A: 1-[1-(6-Chloro-2,3,4,9-tetrahydro-1H-β-carbolin-1-yl)cyclobutyl]-1-propanol 2.32 g of the compound obtained in Step A of Example 115 in 150 ml of tetrahydrofuran are stirred for 4 hours at −30° C., under an inert atmosphere, in the presence of 15 ml of a 1M solution of ethylmagnesium bromide in tetrahydrofuran. After returning to ambient temperature, the mixture is worked up in conventional manner, then concentrated under reduced pressure, enabling the expected product to be isolated.

Step B: 1-[1-(6-Chloro-2,3,4,9-tetrahydro-1H-β-carbolin-1-yl)cyclobutyl]-1-propanone 1 g of the compound obtained in Step A is treated in accordance with the protocol of Step A of Example 115, enabling the expected product to be obtained.

Melting point: 168–170° C. (decomposition); Elemental microanalysis:

|  | C | H | N | Cl |
|---|---|---|---|---|
| % calculated | 61.20 | 6.28 | 7.93 | 20.07 |
| % found | 61.31 | 6.44 | 7.65 | 20.02 |

PHARMACOLOGICAL STUDY OF THE COMPOUNDS OF THE INVENTION

EXAMPLE 117

Penile Erection Test in the Rat, with Erection Induced by Ro 60-0175 (1.25 mg/kg, s.c.)

This test (Eur. J. Pharma., 1997, 325, 9–12) enables evaluation of the capacity of pharmacological agents to inhibit penile erections induced by the administration of Ro 60-0175, a selective 5-HT$_{2C}$ agonist. Inhibition is thus predictive of an antagonist activity in respect of 5-HT$_{2C}$ receptors. Male rats of the Wistar line (Iffa-Credo, France), weighing 120–140 g on the day of the experiment, are placed individually into plexiglass observation boxes (7.5× 18×30 cm) having just been administered the product or its carrier. Thirty minutes later, the animals are administered Ro 60-0175 (1.25 mg/kg, s.c.) and the number of erections achieved in the course of the following 30 minutes is counted. In that test, the $ID_{50}$s (inhibitory dose$_{50}$ expressed in mg/kg, s.c.) exhibited by the compounds of the invention in respect of the products of Examples 1, 6, 7 and 18 are 0.9, 0.9, 1.1 and 0.5 respectively. The compounds of the present invention thus exhibit a powerful activity in that field.

EXAMPLE 118

Antagonist $5HT_{2B}$ Activity

Membranes were prepared from CHO-5-$HT_{2B}$ cells expressing the human $5HT_{2B}$ serotonin receptor, resuspended in assay buffer (Tris-HCl 50 mM, pH=7.4, $CaCl_2$, 4 mM), and stored at −80° C. until use. For binding experiments, 400 µl membrane suspension (50 µg prot/ml final concentration) were incubated with 50 µl [$^3$H]-LSD (1 nM final concentration) and 50 82 l of competing drug for 1 hour at 37° C. Filtration was performed on GF/B Unfilters preincubated in 0.1% polyethyleneimine. In the test, the compounds of the invention show antagonist $5HT_{2B}$ activity and exhibit $IC_{50}$ in the region of nanomolar.

EXAMPLE 119

Pharmaceutical Composition: Tablets

Formulation for the preparation of 1000 tablets each containing 5 mg of active ingredient

| | |
|---|---|
| compound of Example 1 | 5 g |
| hydroxypropyl cellulose | 2 g |
| wheat starch | 10 g |
| lactose | 100 g |
| magnesium stearate | 2 g |
| talc | 2 g |

What is claimed is:
1. A compound selected from those of formula (I):

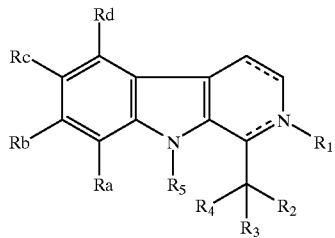

(I)

wherein

==== represents a single or double bond capable optionally of conferring aromatic character to the ring carrying them, $R_1$ represents a group selected from:
hydrogen
linear or branched ($C_1$–$C_6$)alkyl,
—$R_6$-aryl, —$R_6$-cycloalkyl, —$R_6$-imidazolyl, in which $R_6$ represents linear or branched ($C_1$–$C_6$)alkylene,
—$CO_2R_7$ wherein $R_7$ represents linear or branched ($C_1$–$C_6$)alkyl, aryl, cycloalkyl, imidazolyl, —$R_6$-aryl, —$R_6$-cycloalkyl, or —$R_6$-imidazolyl, wherein $R_6$ is as defined hereinbefore,
—$COR_8$ wherein $R_8$ represents hydrogen, linear or branched ($C_1$–$C_6$)alkyl, aryl, cycloalkyl, imidazolyl, —$R_6$-aryl, —$R_6$-cycloalkyl, or —$R_6$-imidazolyl, wherein $R_6$ is as defined hereinbefore, and
—CONH—$R_8$ wherein $R_8$ is as defined hereinbefore,
or $R_1$ does not exist when the nitrogen atom carrying it is already carrying an intracyclic double bond,
$R_2$ represents a group selected from:
cyano,
—$CO_2R_8$ wherein $R_8$ is as defined hereinbefore,
—$CONHR_8$ is as defined hereinbefore,
mono($C_1$–$C_6$)alkylamino($C_1$–$C_6$)alkylaminocarbonyl,
di($C_1$–$C_6$)alkylamino-($C_1$–$C_6$)-alkylaminocarbonyl, alkyl moieties of each of which groups are linear or branched,
—$NR_8R_9$ wherein $R_8$ is as defined hereinbefore and $R_9$ represents a group as defined for $R_8$,
—NH—$CO_2R_7$ wherein $R_7$ is as defined hereinbefore, and
—$COR_8$ wherein $R_8$ is as defined hereinbefore,
$R_3$ and $R_4$ together form ($C_3$–$C_{10}$)cycloalkyl,
$R_5$ represents hydrogen, linear or branched ($C_1$–$C_6$)alkyl, or aryl-($C_1$–$C_6$)alkyl in which alkyl is linear or branched,
Ra, Rb, Rc and Rd, which may be identical or different, each represents, independently of the others, a group selected from hydrogen, halogen, linear or branched ($C_1$–$C_6$)alkyl, hydroxy, linear or branched ($C_1$–$C_6$) alkoxy, linear or branched trihalo-($C_1$–$C_6$)alkyl, linear or branched trihalo-($C_1$–$C_6$)alkoxy, nitro, cyano, amino, linear or branched ($C_1$–$C_6$)alkylamino, di(($C_1$–$C_6$)alkylamino in which each alkyl moiety is linear or branched, aryl, aryl-($C_1$–$C_6$)alkyl in which alkyl is linear or branched, carboxy, linear or branched ($C_1$–$C_6$)alkylcarbonyloxy, linear or branched ($C_1$–$C_6$) acyl, aryloxy, and aryl-($C_1$–$C_6$)alkoxy in which alkoxy is linear or branched,
its isomers, and pharmaceutically-acceptable acid or base addition salt thereof,
it being understood that:
"cycloalkyl" is a mono- or bi-cyclic ring system that is saturated or optionally contains one or more unsaturations that do not confer aromatic character to the ring, contains 3 to 10 carbon, and is optionally substituted by one or more, identical or different, groups selected from halogen, hydroxy, linear or branched ($C_1$–$C_6$)alkyl, and linear or branched ($C_1$–$C_6$)alkoxy,
"aryl" is phenyl, naphthyl, tetrahydronaphthyl, dihydronaphtyl, indenyl or indanyl, each of those groups being optionally substituted by one or more, identical or different, groups selected from halogen, hydroxy, cyano, nitro, linear or branched ($C_1$–$C_6$)alkyl, linear or branched ($C_1$–$C_6$)alkoxy, amino, linear or branched ($C_1$–$C_6$)alkylamino,
di($C_1$–$C_6$)alkylamino, in which each of the alkyl moieties is linear or branched, aryloxy, aryl-($C_1$–$C_6$)alkoxy in which the alkoxy moiety is linear or branched, linear or branched trihalo($C_1$–$C_6$)alkyl, linear or branched ($C_1$–$C_6$)acyl, linear or branched ($C_1$–$C_6$) alkoxycarbonyl, linear or branched ($C_1$–$C_6$) alkylaminocarbonyl, and oxo,
"imidazolyl" is optionally substituted by one or more, identical or different, groups selected from halogen, hydroxy, linear or branched $(C_1-C_6)$alkyl, linear or branched $(C_1-C_6)$alkoxy, nitro, and amino optionally substituted by one or two linear or branched $(C_1-C_6)$ alkyl.

2. A compound of claim 1, wherein $R_3$ and $R_4$ together form saturated monocyclic $(C_3-C_{10})$cycloalkyl optionally substituted by one or more, identical or different, groups selected from halogen, hydroxy, linear or branched $(C_1-C_6)$ alkyl, and linear or branched $(C_1-C_6)$alkoxy.

3. A compound of claim 1, wherein $R_3$ and $R_4$ together form unsubstituted saturated monocyclic $(C_4-C_6)$ cycloalkyl.

4. A compound of claims 1, wherein $R_3$ and $R_4$ together form cyclobutyl.

5. A compound of claim 1, wherein $R_1$ represents hydrogen, or —$COR_8$ wherein $R_8$ is as defined for formula (I).

6. A compound of claim 1, wherein $R_1$ represents —$COR_{8a}$ wherein $R_{8a}$ represents aryl, or imidazolyl.

7. A compound of claim 1, wherein $R_2$ represents —$CO_2R_8$ wherein $R_8$ is as defined for formula (I).

8. A compound of claim 1, wherein $R_2$ represents —$CO_2R_{8b}$ wherein $R_{8b}$ represents linear or branched $(C_1-C_6)$alkyl, or cycloalkyl.

9. A compound of claim 1, wherein $R_2$ represents —$CO_2R_{8b}$ wherein $R_{8b}$ represents ethyl, or cyclopentyl.

10. A compound of claim 1, wherein $R_5$ represents hydrogen.

11. A compound of claim 1, having formula (I'):

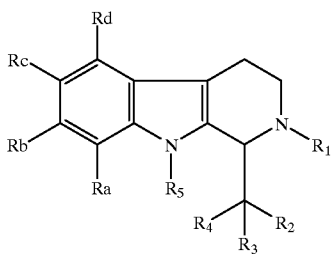

(I')

wherein $R_1$, $R_2$, $R_3$, $R_4$, $R_5$, Ra, Rb, Rc and Rd are as defined for formula (I).

12. A compound of claim 1 which is cyclopentyl 1-(6-chloro-2,3,4,9-tetrahydro-1H-β-carbonlin-1-yl) cyclobutanecarboxylate, its isomers, and pharmaceutically-acceptable acid or base addition salt thereof.

13. A compound of claim 1 which is ethyl 1-(6-bromo-2,3,4,9-tetrahydro-1H-β-carbonlin-1-yl) cyclobutanecarboxylate, its isomers, and pharmaceutically-acceptable acid or base addition salt thereof.

14. A compound of claim 1 which is ethyl 1-[6-chloro-2-(1H-imidazol-5-ylcarbonyl)-2,3,4,9-tetrahydro-1H-β-carbonlin-1-yl]cyclobutanecarboxylate, its isomers, and pharmaceutically-acceptable acid or base addition salt thereof.

15. A compound of claim 1 which is ethyl 1-(6-methyl-2,3,4,9-tetrahydro-1H-β-carbonlin-1-yl) cyclobutanecarboxylate, its isomers, and pharmaceutically-acceptable acid or base addition salt thereof.

16. A compound of claim 1 which is ethyl 1-(5,6-dichloro-2,3,4,9-tetrahydro-1H-β-carbonlin-1-yl) cyclobutanecarboxylate, its isomers, and pharmaceutically-acceptable acid or base addition salt thereof.

17. A compound of claim 1 which is ethyl 1-(6-chloro-2,3,4,9-tetrahydro-1H-β-carbonlin-1-yl) cyclobutanecarboxylate, its isomers, and pharmaceutically-acceptable acid or base addition salt thereof.

18. A compound of claim 1 which is ethyl 1-(6,7-dichloro-2,3,4,9-tetrahydro-1H-β-carbonlin-1-yl) cyclobutanecarboxylate, its isomers, and pharmaceutically-acceptable acid or base addition salt thereof.

19. A compound of claim 1 which is ethyl 1-(6-methoxy-2,3,4,9-tetrahydro-1H-β-carbonlin-1-yl) cyclobutanecarboxylate, its isomers, and pharmaceutically-acceptable acid or base addition salt thereof.

20. A method for treating a living body afflicted with a condition selected from depression and anxiety, comprising the step of administering to the living body an amount of a compound of claim 1 which is effective for alleviation of said condition.

21. A pharmaceutical composition useful in the treatment of CNS disorders comprising as active principle an effective amount of a compound as claimed in claim 1, together with one or more pharmaceutically-acceptable excipients or vehicles.

* * * * *